United States Patent
Bachmann et al.

(10) Patent No.: US 9,975,856 B2
(45) Date of Patent: May 22, 2018

(54) PROCESS FOR THE PREPARATION OF (E)-3-(4-((E)-2-(2-CHLORO-4-FLUOROPHENYL)-1-(1H-INDAZOL-5-YL)BUT-1-EN-1-YL)PHENYL)ACRYLIC ACID

(71) Applicant: Genentech, Inc., South San Francisco, CA (US)

(72) Inventors: Stephan Bachmann, Basel (CH); Serena Maria Fantasia, Basel (CH); Francis Gosselin, San Mateo, CA (US); Chong Han, Foster City, CA (US); Stefan Hildbrand, Basel (CH); Theresa Humphries, San Francisco, CA (US); Christian Jenny, Basel (CH); Ngiap-Kie Lim, South San Francisco, CA (US); Andrew McClory, South San Francisco, CA (US); Christian Moessner, Basel (CH); Pankaj Rege, Basel (CH); Scott Savage, Burlingame, CA (US); Haiming Zhang, San Mateo, CA (US)

(73) Assignee: Genentech, inc., South San Francisco, CA (US)

( * ) Notice: Subject to any disclaimer, the term of this patent is extended or adjusted under 35 U.S.C. 154(b) by 0 days. days.

(21) Appl. No.: 15/287,023

(22) Filed: Oct. 6, 2016

(65) Prior Publication Data
US 2017/0101380 A1    Apr. 13, 2017

Related U.S. Application Data

(60) Provisional application No. 62/238,230, filed on Oct. 7, 2015.

(51) Int. Cl.
| C07D 231/56 | (2006.01) |
| C07D 405/04 | (2006.01) |
| C07C 309/73 | (2006.01) |
| C07C 69/73 | (2006.01) |
| C07F 5/04 | (2006.01) |
| C07C 69/612 | (2006.01) |
| C07F 5/02 | (2006.01) |

(52) U.S. Cl.
CPC .......... *C07D 231/56* (2013.01); *C07C 69/612* (2013.01); *C07C 69/73* (2013.01); *C07C 309/73* (2013.01); *C07D 405/04* (2013.01); *C07F 5/025* (2013.01); *C07F 5/04* (2013.01)

(58) Field of Classification Search
None
See application file for complete search history.

(56) References Cited

U.S. PATENT DOCUMENTS

| 8,299,112 | B2 | 10/2012 | Smith |
| 8,455,534 | B2 | 6/2013 | Smith |
| 9,399,646 | B2 | 7/2016 | Smith |
| 9,499,538 | B2 | 11/2016 | Smith |
| 2012/0071535 | A1 | 3/2012 | Smith |
| 2013/0012561 | A1 | 1/2013 | Smith |
| 2013/0231333 | A1 | 9/2013 | Smith |
| 2015/0105403 | A1 | 4/2015 | Smith |
| 2015/0157606 | A1 | 6/2015 | Maneval |
| 2015/0258080 | A1 | 9/2015 | Hager |
| 2015/0258099 | A1 | 9/2015 | Hager |
| 2016/0039770 | A1 | 2/2016 | Smith |

FOREIGN PATENT DOCUMENTS

| WO | 2012/037410 A2 | 3/2012 |
| WO | 2012/037411 A2 | 3/2012 |
| WO | 2013/142266 A1 | 9/2013 |
| WO | 2014/151899 A1 | 9/2014 |

OTHER PUBLICATIONS

Govek et al., "Optimization of an indazole series of selective estrogen receptor degraders: Tumor regression in a tamoxifen-resistant breast cancer xenograft" Bioorg Med Chem Lett. 25(22):5163-7 ( 2015).
Groheux et al., "Estrogen Receptor-Positive/Human Epidermal Growth Factor Receptor 2-Negative Breast Tumors" Cancer 119(11):1960-68 ( 2013).
ISR for PCT/EP2016/073831.
Lai et al., "Identification of GDC-0810 (ARN-810), an Orally Bioavailable Selective Estrogen Receptor Degrader (SERD) that Demonstrates Robust Activity in Tamoxifen-Resistant Breast Cancer Xenografts" Journal of Medicinal Chemistry 58(12):4888-4904 ( 2015).
Lips et al., "Neoadjuvant chemotherapy in ER+ HER2− breast cancer:response prediction based on immunohistochemical and molecular characteristics" Breast Cancer Res Treat 131:827-36 (Apr. 2011).

*Primary Examiner* — Kamal Saeed
(74) *Attorney, Agent, or Firm* — Kevin M. Clark

(57) ABSTRACT

Processes are described for the preparation of estrogen receptor modulating compound, (E)-3-(4-((E)-2-(2-chloro-4-fluorophenyl)-1-(1H-indazol-5-yl)but-1-en-1-yl)phenyl) acrylic acid I:

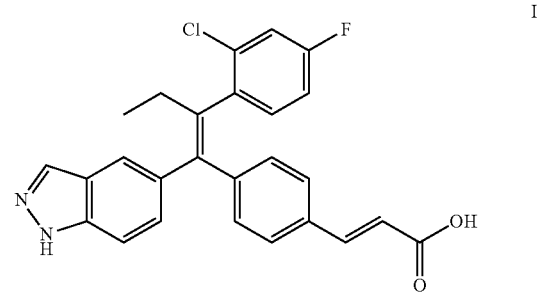

and salts thereof, and intermediates useful for the preparation of I.

13 Claims, No Drawings

PROCESS FOR THE PREPARATION OF (E)-3-(4-((E)-2-(2-CHLORO-4-FLUOROPHENYL)-1-(1H-INDAZOL-5-YL)BUT-1-EN-1-YL)PHENYL) ACRYLIC ACID

CROSS REFERENCE TO RELATED APPLICATIONS

This non-provisional application filed under 37 CFR § 1.53(b), claims the benefit under 35 USC § 119(e) of U.S. Provisional Application Ser. No. 62/238,230 filed on 7 Oct. 2015, which is incorporated by reference in entirety.

FIELD OF THE INVENTION

The invention relates to methods of making an estrogen receptor modulating compound, (E)-3-(4-((E)-2-(2-chloro-4-fluorophenyl)-1-(1H-indazol-5-yl)but-1-en-1-yl)phenyl) acrylic acid.

BACKGROUND OF THE INVENTION

The estrogen receptor is a critical driver in breast cancer (Di Cosimo, S. & Baselga, J. (2010) Nat. Rev. Clin. Oncol). Since about 60-70% of breast cancer (BC) is estrogen receptor positive (ER+), modulation of estrogen activity and/or synthesis is the main therapeutic strategy in the treatment of ER+BC. Effective hormonal therapies are used across many lines of therapy to decrease estrogen/ligand (ovarian suppression, aromatase inhibitors). Selective Estrogen Receptor Modulators (SERMs) bind to ER, downregulate ER levels and antagonize ER transcriptional activity. Selective Estrogen Receptor Degraders (SERDs) bind to ER and degrade ER. Many breast cancer patients relapse or develop resistance in their tumors, which are often still dependent on the ER.

The N-methyl-D-glucamine salt of (E)-3-(4-((E)-2-(2-Chloro-4-fluorophenyl)-1-(1H-indazol-5-yl)but-1-en-1-yl) phenyl)acrylic acid (GDC-0810, ARN-810, Seragon Pharmaceuticals, Inc., Genentech Inc., CAS Registry Number 1365888-06-7) is an oral, non-steroidal, estrogen receptor alpha (ERα) antagonist and selective estrogen receptor degrader (SERD) that competes with estrogens for binding to the estrogen receptor with low nanomolar potency (U.S. Pat. No. 8,299,112; U.S. Pat. No. 8,455,534; Lai et al (2015) J. Med. Chem. 58:4888-4904). A Phase I study evaluated the oral selective estrogen receptor degrader GDC-0810 (ARN-810) in postmenopausal women with estrogen receptor positive (ER+) HER2–, advanced/metastatic breast cancer (Zhou et al, "Selective Estrogen Receptor Degrader (SERD) activity in ESR1 mutant models", AACR Poster #1864; Joseph et al, "Discovery of GDC-0810 a novel, non-steroidal selective estrogen receptor degrader with robust activity in pre-clinical models of endocrine-resistant breast cancer", AACR Poster #5053; Dickler M N, et al (2015) AACR Annual Meeting, Clinical Trials of New Drugs in Breast Cancer, Apr. 20, 2015, Abstract CT231). GDC-0810 has demonstrated tumor regression in tamoxifen sensitive and resistant BC models.

In contrast to first generation ER antagonists, such as tamoxifen, GDC-0810 fully antagonizes the response of ER to estrogens and induces proteosomal degradation of ER-α in breast cancer cell lines. These bipartite activities result in full antagonism of ER-target gene transcription in breast cancer cell lines in vitro. The result is robust inhibition of ER signaling, and in turn, inhibition of breast tumor cell proliferation. Unlike fulvestrant, which is also an ER antagonist and degrader, GDC-0810 has a nonsteroidal chemical backbone and displays oral bioavailability.

SUMMARY OF THE INVENTION

The invention relates to methods of making the estrogen receptor modulating compound, (E)-3-(4-((E)-2-(2-chloro-4-fluorophenyl)-1-(1H-indazol-5-yl)but-1-en-1-yl)phenyl) acrylic acid I:

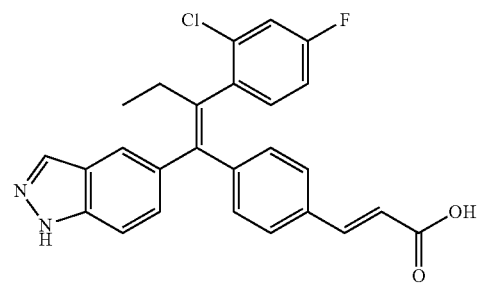

and salts thereof.

An aspect of the invention is a process for the preparation of (E)-3-(4-((E)-2-(2-chloro-4-fluorophenyl)-1-(1H-indazol-5-yl)but-1-en-1-yl)phenyl)acrylic acid I, comprising:

(a) reacting III and malonic acid to form II

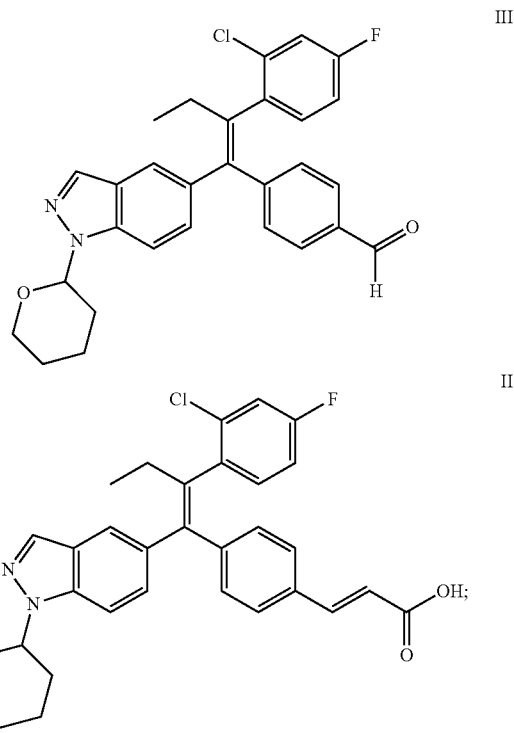

and (b) reacting II with acid to form I.

Another aspect of the invention is a process for (E)-3-(4-((E)-2-(2-chloro-4-fluorophenyl)-1-(1H-indazol-5-yl)but-1-en-1-yl)phenyl)acrylic acid I, comprising:

(a) reacting VI and (E)-tert-butyl 3-(4-bromophenyl)acrylate to form VIII (a) reacting X with an enolization reagent to form XI;

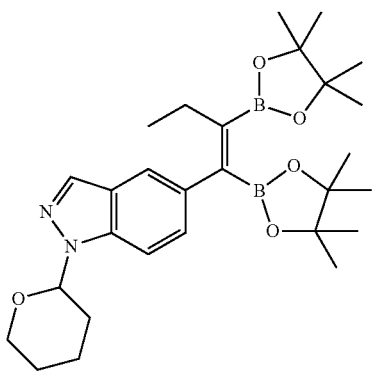
VI

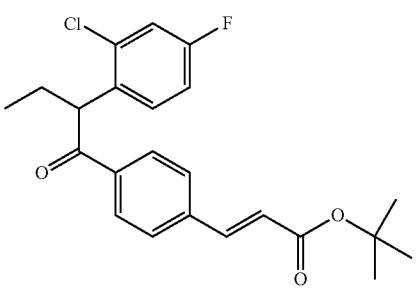
X

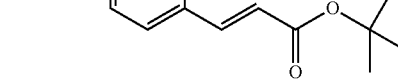
XI where E is selected from para-toluene sulfonate, trifluoromethane sulfonate, methane sulfonate and diphenyl phosphate;

(b) reacting XI with XII and a palladium catalyst to form IX; and

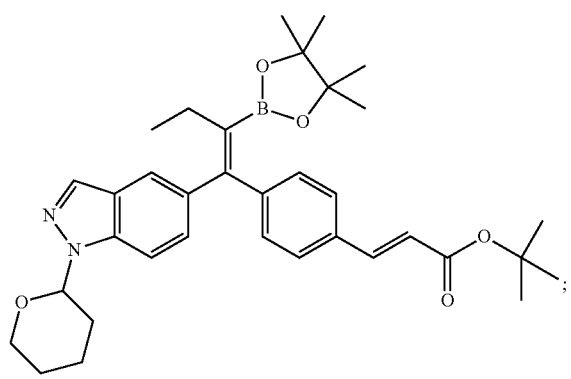
VIII

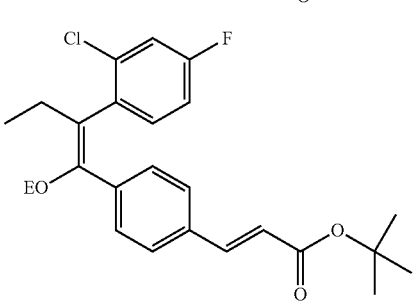
XII (b) reacting VIII with 2-chloro-4-fluoro-1-iodobenzene to form IX

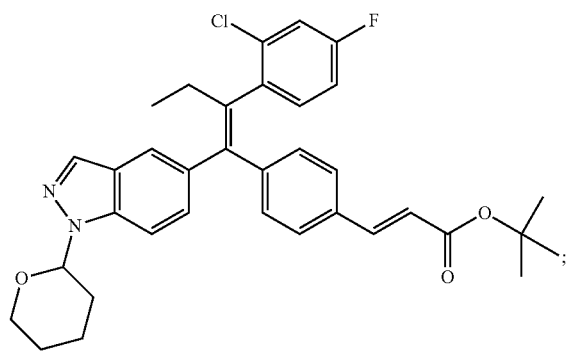
IX

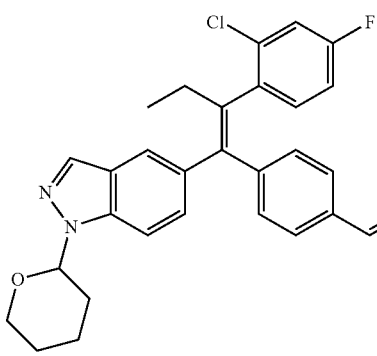
IX and (c) reacting IX with acid to form I.

Another aspect of the invention is a process for (E)-3-(4-((E)-2-(2-chloro-4-fluorophenyl)-1-(1H-indazol-5-yl)but-1-en-1-yl)phenyl)acrylic acid I, comprising:

(c) reacting IX with acid to form I.

Another aspect of the invention is a process for (E)-3-(4-((E)-2-(2-chloro-4-fluorophenyl)-1-(1H-indazol-5-yl)but-1-en-1-yl)phenyl)acrylic acid I, comprising:

(a) reacting XIII with (E)-(4-(3-(tert-butoxy)-3-oxoprop-1-en-1-yl)phenyl)magnesium halide reagent XIV to form XV;

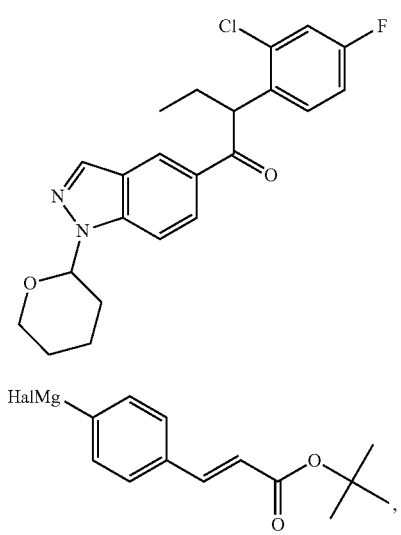

XIII

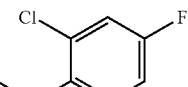

XIV where Hal is Cl, Br, or I,

XV

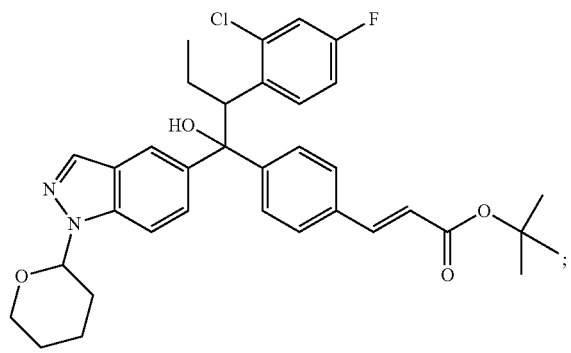

(b) reacting XV with a derivatizing reagent to form XVI;

XVI

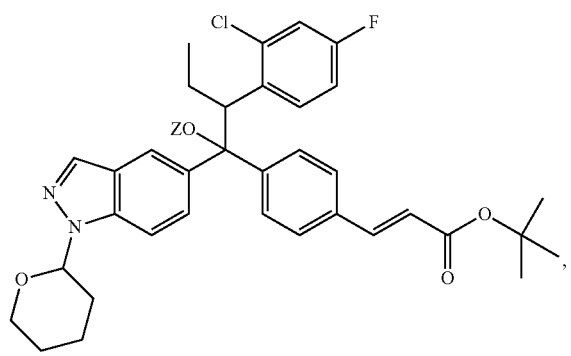

where Z is pivaloyl, t-butoxycarbonyl, isopropyl carbonate, methoxycarbonyl, N,N-dimethyl carbamate, diphenylphosphoryl, isobutyl carbonyl, acetyl, trifluoroacetyl, trifluoroacetyl bis(2-oxo-3-oxazolidinyl)phosphoryl, and diethylphosphoryl;

(c) reacting XVI with base selected from sodium hexamethyldisilazide, potassium carbonate, tributylamine, and 1,4-diazabicyclo[2.2.2]octane to form IX

IX and
(d) reacting IX with aqueous acid to form I.

Another aspect of the invention is a process for (E)-3-(4-((E)-2-(2-chloro-4-fluorophenyl)-1-(1H-indazol-5-yl)but-1-en-1-yl)phenyl)acrylic acid I, comprising: reacting I with an amine base to form XVII;

XVII and
reacting XVII with aqueous acid to form I, where B is the protonated form of diethylamine, N,N-methylcyclohexylamine, azepine, cyclohexylamine, pyrrolidine, N-methylimidazole, triethylamine, N,N-dimethylcyclohexylamine, N-methylpiperidine, diisopropylamine, N-methylpyrrolidine, N-methylmorpholine;

DEFINITIONS

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities.

Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers (stereocenters), and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The phrase "pharmaceutically acceptable salt" as used herein, refers to pharmaceutically acceptable organic or inorganic salts of a compound of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

If the compound of the invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of the invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

A "solvate" refers to an association or complex of one or more solvent molecules and a compound of the invention. Examples of solvents that form solvates include, but are not limited to, water, isopropanol, ethanol, methanol, DMSO, ethyl acetate, acetic acid, and ethanolamine. The term "hydrate" refers to the complex where the solvent molecule is water.

The phrase "pharmaceutically acceptable salt" as used herein, refers to pharmaceutically acceptable organic or inorganic salts of a compound of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

Preparation of (E)-3-(4-((E)-2-(2-Chloro-4-Fluorophenyl)-1-(1H-Indazol-5-Yl)but-1-En-1-Yl)Phenyl) Acrylic Acid The present invention includes processes, methods, reagents, and intermediates for the synthesis of the estrogen receptor modulating compound, (E)-3-(4-((E)-2-(2-chloro-4-fluorophenyl)-1-(1H-indazol-5-yl)but-1-en-1-yl)phenyl) acrylic acid I (CAS Registry Number 1365888-06-7), also known as GDC-0810, ARN810, or (E)-3-[4-[(E)-2-(2-chloro-4-fluorophenyl)-1-(1H-indazol-5-yl)but-1-en-1-yl] phenyl]-2-propenoic acid, and described in (U.S. Pat. No. 8,299,112; U.S. Pat. No. 8,455,534; WO 2012/037411; WO 2012/037410; Lai et al (2015) J. Med. Chem. 58:4888-4904) which are expressly incorporated by reference). As used herein, GDC-0810 includes all stereoisomers, geometric isomers, tautomers, and pharmaceutically acceptable salts thereof.

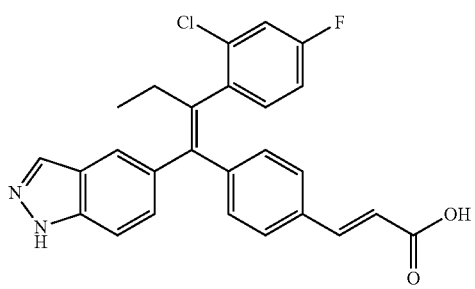

I

GDC-0810, and reagents and intermediates for preparation of GDC-0810, as compounds of the invention, may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. In addition, the present invention embraces all geometric and positional isomers. In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

The compounds of the invention may exist in unsolvated as well as solvated forms with pharmaceutically acceptable solvents such as water, ethanol, and the like, and it is intended that the invention embrace both solvated and unsolvated forms.

The compounds of the invention may also exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The compounds of the invention also include isotopically-labeled compounds which are identical to those recited herein, but for the fact that one or more atoms are replaced by an atom having an atomic mass or mass number different from the atomic mass or mass number usually found in nature. All isotopes of any particular atom or element as specified are contemplated within the scope of the compounds of the invention, and their uses. Exemplary isotopes that can be incorporated into compounds of the invention include isotopes of hydrogen, carbon, nitrogen, oxygen, phosphorus, sulfur, fluorine, chlorine and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{32}P$, $^{33}P$, $^{35}S$, $^{18}F$, $^{36}Cl$, $^{123}I$ and $^{125}I$. Certain isotopically-labeled compounds of the present invention (e.g., those labeled with $^{3}H$ and $^{14}C$) are useful in compound and/or substrate tissue distribution assays. Tritiated ($^{3}H$) and carbon-14 ($^{14}C$) isotopes are useful for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Positron emitting isotopes such as $^{15}O$, $^{13}N$, $^{11}C$ and $^{18}F$ are useful for positron emission tomography (PET) studies to examine substrate receptor occupancy. Isotopically labeled compounds of the present invention can generally be prepared by following procedures analogous to those disclosed in the Examples herein below, by substituting an isotopically labeled reagent for a non-isotopically labeled reagent.

Starting materials and reagents for the preparation of GDC-0810 are generally available from commercial sources or are readily prepared using methods well known to those skilled in the art (e.g., prepared by methods generally described in Louis F. Fieser and Mary Fieser, *Reagents for Organic Synthesis*, v. 1-19, Wiley, N.Y. (1967-1999 ed.), or *Beilsteins Handbuch der organischen Chemie*, 4, Aufl. ed. Springer-Verlag, Berlin, including supplements (also available via the Beilstein online database).

The following Schemes 1-13 illustrate the chemical reactions, processes, methodology for the synthesis of GDC-0810, Formula I, and certain intermediates and reagents.

Scheme 1:

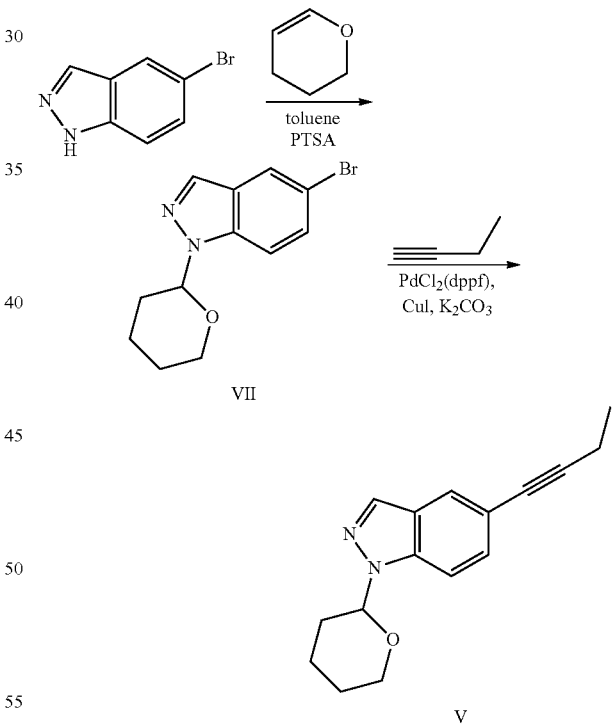

Scheme 1 shows conversion of 5-bromo-1H-indazole to 5-(but-1-yn-1-yl)-1-(tetrahydro-2H-pyran-2-yl)-1H-indazole V (Examples 1 and 2). This process to prepare V is superior as an improvement over methods described in WO 2012/037410 and WO 2012/037411. In particular, WO 2012/037410 and WO 2012/037411 teach reacting V with trimethylsilylacetylene under Sonogashira cross-coupling conditions, followed by metalation of the acetylene proton and alkylation with iodoethane. The method of Scheme 1 has the advantage of avoiding the expensive trimethylsilylacetylene reagent and adding the but-1-yn-1-yl group directly and in one step to VII.

While PdCl₂(dppf) is an effective catalyst or catalyst precursor for the reaction, other types of palladium catalysts or catalyst precursors can also be used. A Pd(II) complex is the catalyst precursor of the active catalyst, Pd(O) complex. 1,1'-Bis(diphenylphosphino)ferrocene (dppf), is an organophosphorus compound commonly used as a ligand in homogeneous catalysis. Nonlimiting examples of palladium catalysts or catalyst precursors include Pd₂(dba)₃, Na₂PdCl₄, and Pd(OAc)₂. While dppf is an effective ligand for the reaction, other types of ligands (monodentate or bidentate) can also be used.

Nonlimiting examples of such ligands include P(t-Bu)₃, P(o-Tol)3, as well as nonphosphorous ligands. The active catalyst is a Pd(O) catalyst which can be generated by using a Pd(O) source such as Pd2(dba)3 or Pd(PPh3)4 and a mono or bidentate ligand such as PR3 or dppf (and others) or the Pd(O) species can be generated in situ from a Pd(II) source such as Pd(OAc)2, Na2PdCl4 with a mono or bidentate phosphine such as PPh3, P(tBu)3, P(o-Tol)3, dppf, dppe (1,2-diphenylphosphinoethane).

While K₂CO₃ is an effective base for the reaction, other types of bases can also be used. Nonlimiting examples of such bases include Et₃N, Et₂NH, pyrrolidine, i-Pr₂NH, N,N-diisopropylethylamine, morpholine, and Cs₂CO₃. A variety of solvents can be used in Sonogashira reaction, such as DMF, THF, 2-Me-THF, CH₃CN, DMSO, toluene, and 1,4-dioxane.

Scheme 2:

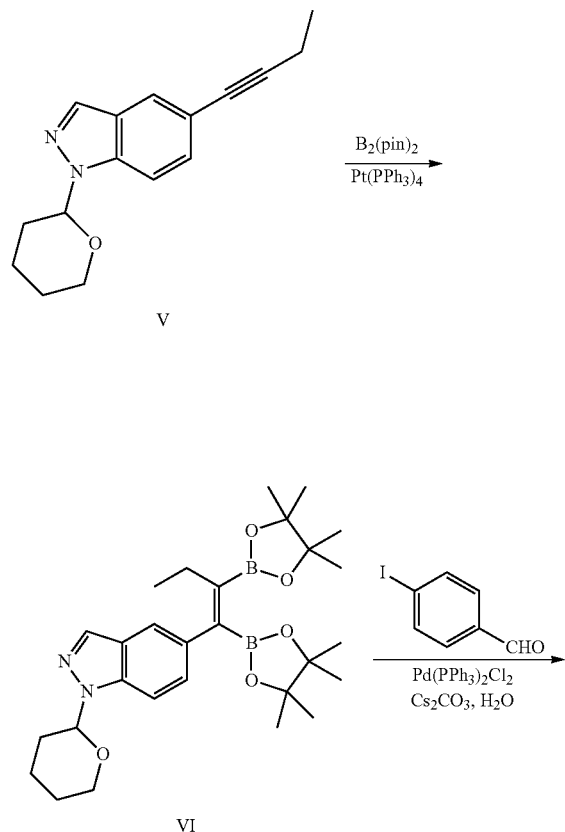

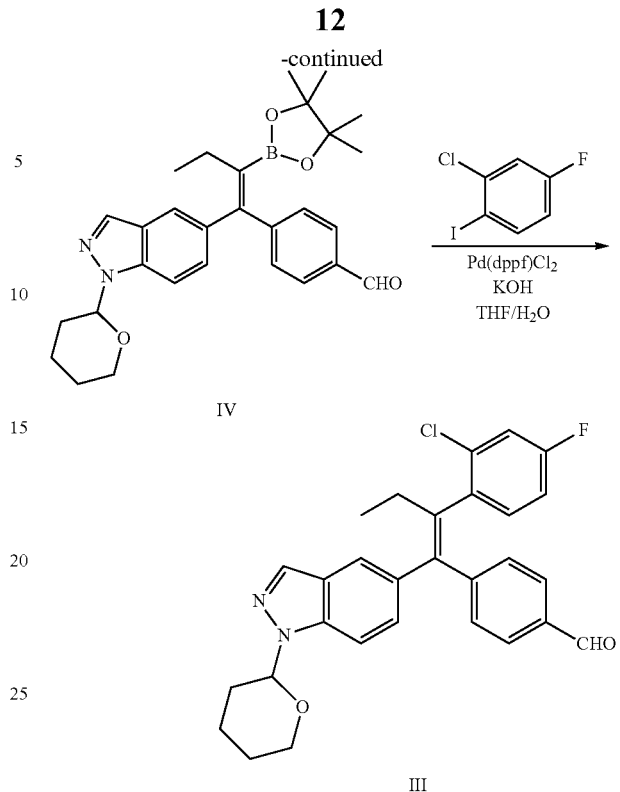

Scheme 2 shows conversion of 5-(but-1-yn-1-yl)-1-(tetrahydro-2H-pyran-2-yl)-1H-indazole V to (E)-4-(2-(2-chloro-4-fluorophenyl)-1-(1-(tetrahydro-2H-pyran-2-yl)-1H-indazol-5-yl)but-1-en-1-yl)benzaldehyde III (Examples 3-5). This process to prepare III and IV is superior as an improvement over methods described in WO 2012/037410 (pages 70 and 71) and WO 2012/037411.

Borylation of V proceeds with 4,4,4',4',5,5,5',5'-octamethyl-2,2'-bi(1,3,2-dioxaborolane) (bis(pinacolato)diboron (BzPinz) under platinum catalysis to give (Z)-5-(1,2-bis(4,4,5,5-tetramethyl-1,3,2-dioxaborolan-2-yl)but-1-en-1-yl)-1-(tetrahydro-2H-pyran-2-yl)-1H-indazole VI (Example 3). Other borylation reagents and conditions may be used, such as 2,3-dimethylbutane-2,3-diol (pinacol) and naphthalene-1,8-diamine (Sugimome, et al (2010) Jour. Am. Chem. Soc. 132:2548); and B₂Pin₂ and 1,1'-azanediylbis(propan-2-ol) to form (4R,8R)-4,6,8-trimethyl-2-(4,4,5,5-tetramethyl-1,3,2-dioxaborolan-2-yl)-1,3,6,2-dioxazaborocane (Santos, et al (2011) Jour. Org. Chem. 76:3397).

Reaction of VI with 4-bromobenzaldehyde (or 4-iodobenzaldehyde) under palladium catalysis gives (Z)-4-(1-(1-(tetrahydro-2H-pyran-2-yl)-1H-indazol-5-yl)-2-(4,4,5,5-tetramethyl-1,3,2-dioxaborolan-2-yl)but-1-en-1-yl)benzaldehyde IV (Example 4).

While PdCl₂ (dppf) is an effective catalyst for the reaction to prepare III from IV, other types of palladium catalysts or catalyst precursors may be useful for the reaction such as PdCl₂(PPh₃)₂, Pd(t-Bu)₃, PdCl₂ dppf CH₂Cl₂, Pd(PPh₃)₄, Pd(OAc)/PPh₃, Cl₂Pd[(Pet₃)]₂, Pd(DIPHOS)₂, Cl₂Pd(Bipy), [PdCl(Ph₂PCH₂PPh₂)]₂, Cl₂Pd[P(o-tol)₃]₂, Pd₂(dba)₃/P(o-tol)₃, Pd₂(dba)/P(furyl)₃, Cl₂Pd[P(furyl)₃]₂, Cl₂Pd(PMePh₂)₂, Cl₂Pd[P(4-F-Ph)₃]₂, Cl₂Pd[P(C₆F₆)₃]₂, Cl₂Pd[P(2-COOH-Ph)(Ph)₂]₂, Cl₂Pd[P(4-COOH-Ph)(Ph)₂]₂, and encapsulated catalysts Pd EnCat™ 30, Pd EnCat™ TPP30, and Pd(II)EnCat™ BINAP30, according to procedures analogous to those described in J. Tsuji, "Transition Metal Reagents and Catalysts, Innovations in Organic Synthesis", John Wiley & sons, Chichester, 2000 and references cited therein. Palladium catalyzed reactions may be conducted in the presence of organic solvents such as THF, tert-butylmethyl ether, 2-methyltetrahydrofuran, dibutyl ether, cyclopentylmethyl ether, dimethyl acetal or dioxane, N,N-dimethylformamide and N-methylpyrrolidone, and with bases such as $K_3PO_4$, $K_2CO_3$, $KHCO_3$, $Cs_2CO_3$, KOH, NaOH, trimethylamine, tripropylamine, N,N-diethylpropylamine, N,N-diisopropylethylamine, and N-methylmorpholine.

Scheme 3:

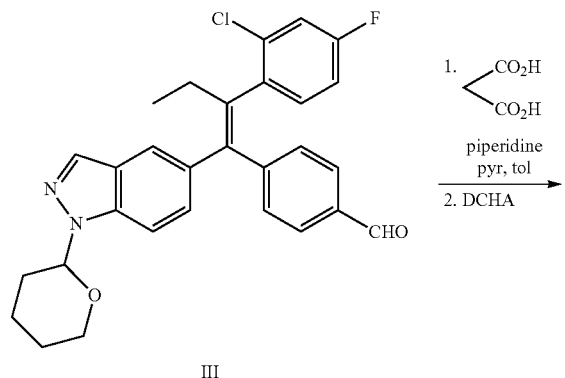

III

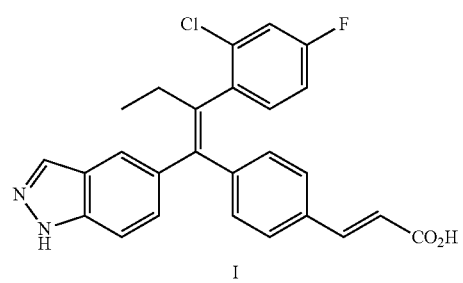

II

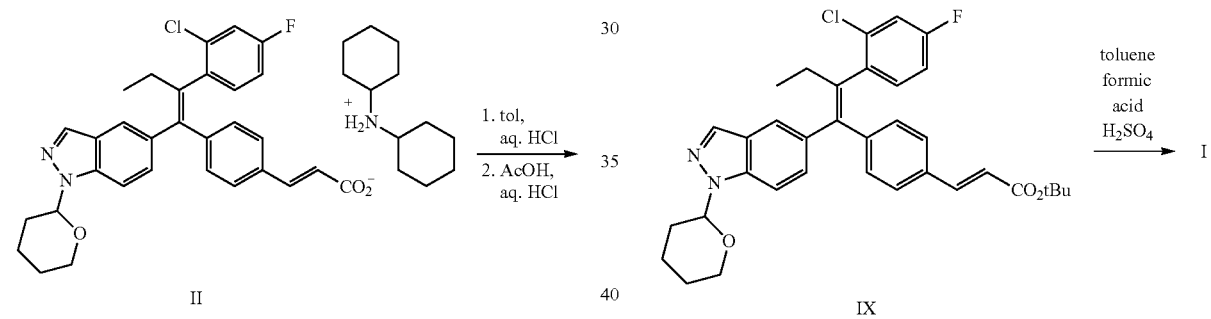

I

Scheme 3 shows conversion of (E)-4-(2-(2-chloro-4-fluorophenyl)-1-(1-(tetrahydro-2H-pyran-2-yl)-1H-indazol-5-yl)but-1-en-1-yl)benzaldehyde III to (E)-3-(4-((E)-2-(2-chloro-4-fluorophenyl)-1-(1H-indazol-5-yl)but-1-en-1-yl)phenyl)acrylic acid I (Examples 6 and 7). Intermediate III was treated with malonic acid, piperidine, and pyridine in toluene. Addition of dicyclohexylamine gave dicyclohexylammonium (E)-3-(4-((E)-2-(2-chloro-4-fluorophenyl)-1-(1-(tetrahydro-2H-pyran-2-yl)-1H-indazol-5-yl)but-1-en-1-yl)phenyl)acrylate II. The THP group was removed with aqueous acid in a solvent such as toluene. The aqueous acid may be, but not limited to, formic acid, hydrochloric acid, or sulfuric acid.

Scheme 4:

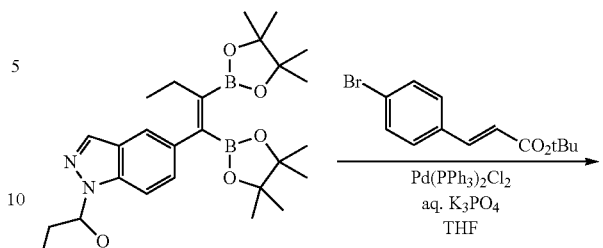

VI

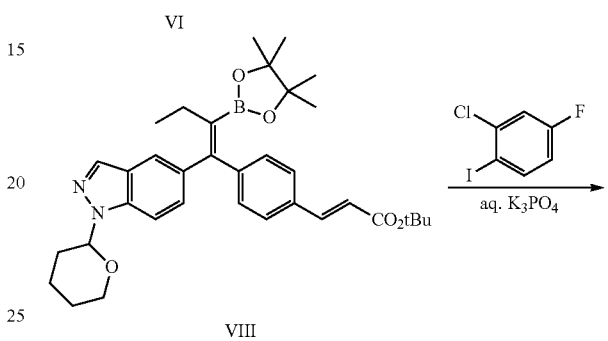

VIII

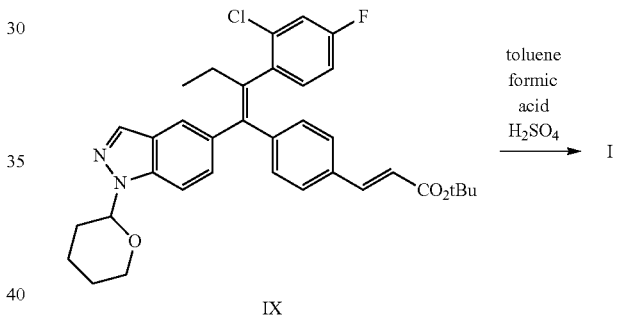

IX

Scheme 4 shows conversion of (Z)-5-(1,2-bis(4,4,5,5-tetramethyl-1,3,2-dioxaborolan-2-yl)but-1-en-1-yl)-1-(tetrahydro-2H-pyran-2-yl)-1H-indazole VI to (E)-3-(4-((E)-2-(2-chloro-4-fluorophenyl)-1-(1H-indazol-5-yl)but-1-en-1-yl)phenyl)acrylic acid I (Examples 8 and 9). Intermediate VI was reacted with (E)-tert-butyl 3-(4-bromophenyl)acrylate and bis(triphenylphosphine)palladium(II) dichloride in tetrahydrofuran, potassium phosphate tribasic and water to give (E)-tert-butyl 3-(4-((Z)-1-(1-(tetrahydro-2H-pyran-2-yl)-1H-indazol-5-yl)-2-(4,4,5,5-tetramethyl-1,3,2-dioxaborolan-2-yl)but-1-en-1-yl)phenyl)acrylate VIII. Alternatively, cesium carbonate can be used as the base in conversion of Intermediate VI to VIII. Intermediate VIII was reacted with 2-chloro-4-fluoroiodobenzene, bis(triphenylphosphine)palladium(II) dichloride in aqueous potassium phosphate or alternatively in 1.0 M potassium hydroxide (Example 8) to give (E)-tert-butyl 3-(4-((E)-2-(2-chloro-4-fluorophenyl)-1-(1-(tetrahydro-2H-pyran-2-yl)-1H-indazol-5-yl)but-1-en-1-yl)phenyl)acrylate IX. Intermediate IX was treated with formic acid and sulfuric acid in water and toluene (Example 9), or alternatively with aqueous hydrochloric acid and methanol to give (E)-3-(4-((E)-2-(2-chloro-4-fluorophenyl)-1-(1H-indazol-5-yl)but-1-en-1-yl)phenyl)acrylic acid I.

Scheme 5

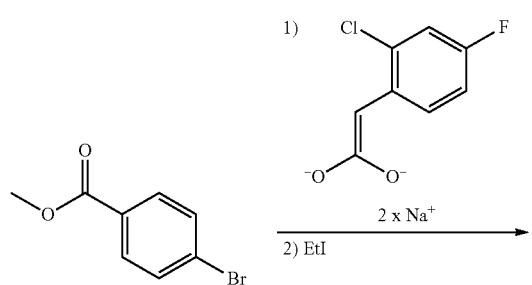

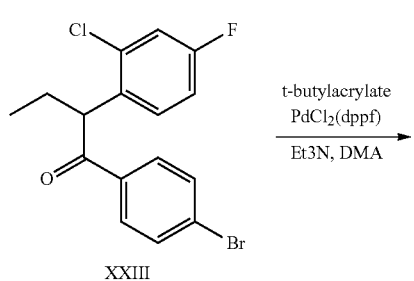

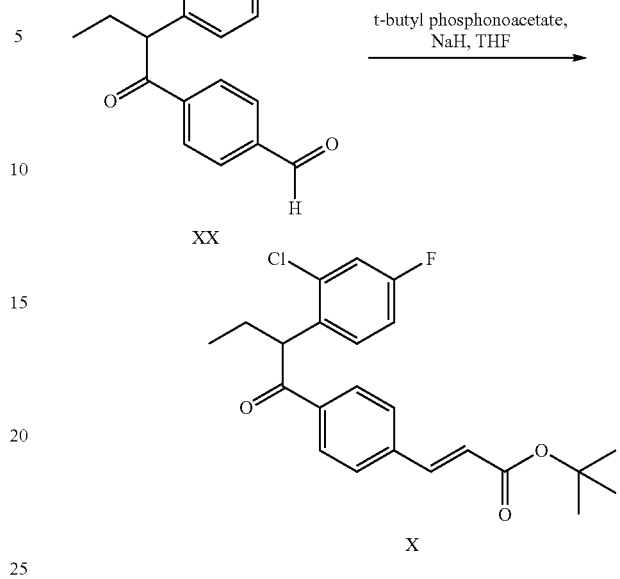

Scheme 5 shows conversion of methyl 4-bromobenzoate (CAS#619-42-1) to tert-butyl (E)-3-(4-(2-(2-chloro-4-fluorophenyl)butanoyl)phenyl)acrylate X (Example 10). The dianion of 2-chloro-4-fluorophenylacetic acid acylates methyl 4-bromobenzoate to give 1-(4-bromophenyl)-2-(2-chloro-4-fluorophenyl)butan-1-one XXIII which is reacted under Heck reaction conditions with tert-butyl acrylate and palladium catalysis to give X. Methyl 4-iodobenzoate can also be used to form XXIII Scheme 6

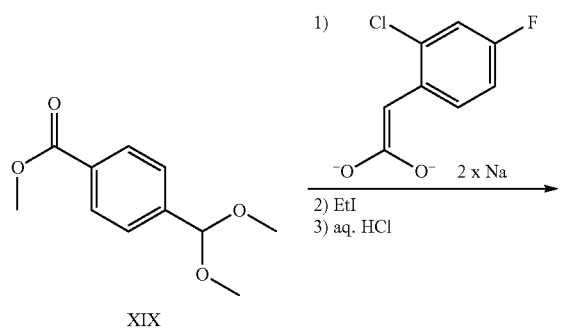

Scheme 6 shows conversion of methyl 4-formylbenzoate dimethylacetal XIX to tert-butyl (E)-3-(4-(2-(2-chloro-4-fluorophenyl)butanoyl)phenyl)acrylate X (Example 11). Acylation of the disodium salt of 2-chloro-4-fluorophenylacetic acid with methyl 4-formylbenzoate dimethyl acetal XIX, alkylation of the intermediate with iodoethane and hydrolysis of the dimethyl acetal gave 4-(2-(2-chloro-4-fluorophenyl)butanoyl)benzaldehyde XX. Reaction of XX with tert-butyldiethylphosphonoacetate in the presence of sodium hydride gave X.

Scheme 7:

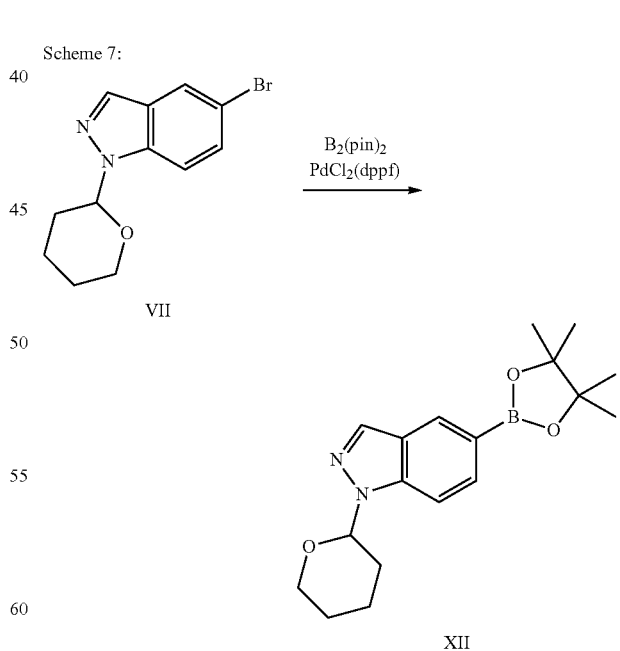

Scheme 7 shows conversion of 5-bromo-1-(tetrahydro-2H-pyran-2-yl)-1H-indazole VII to 1-(tetrahydro-2H-pyran-2-yl)-5-(4,4,5,5-tetramethyl-1,3,2-dioxaborolan-2-yl)-1H-indazole XII according to Example 12. Alternatively, VII can be borylated with 2-isopropoxy-4,4,5,5-tetramethyl-1,3,2-dioxaborolane according to Example 13)
Scheme 8
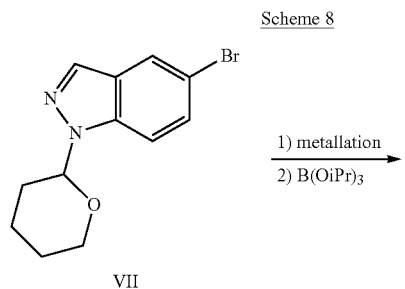
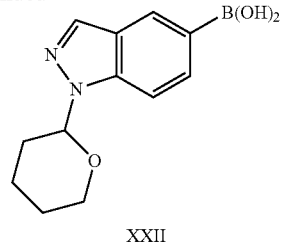
Scheme 8 shows conversion of 5-bromo-1-(tetrahydro-2H-pyran-2-yl)-1H-indazole VII to (1-(tetrahydro-2H-pyran-2-yl)-1H-indazol-5-yl)boronic acid XXII (Examples 14 and 15).
Scheme 9:
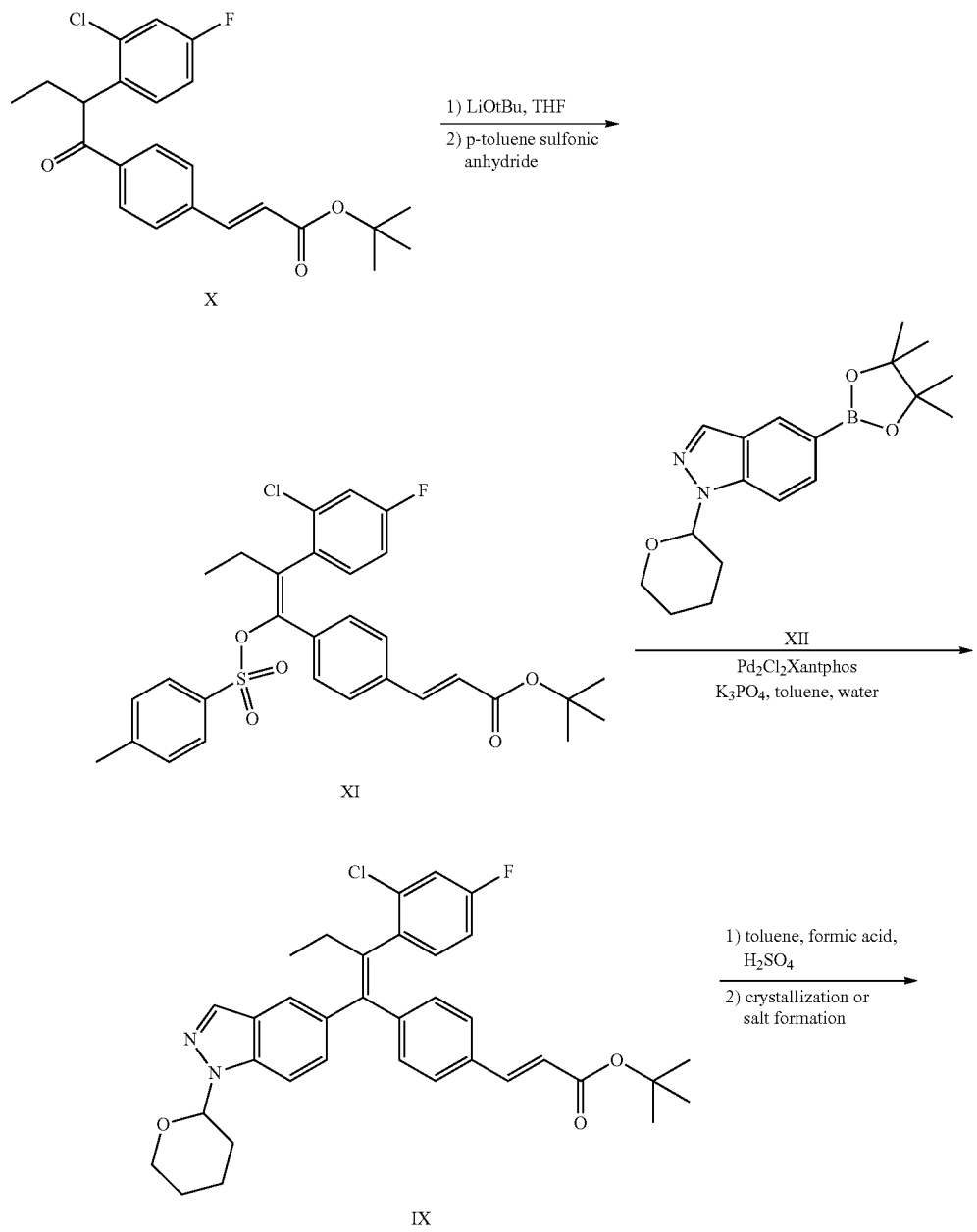

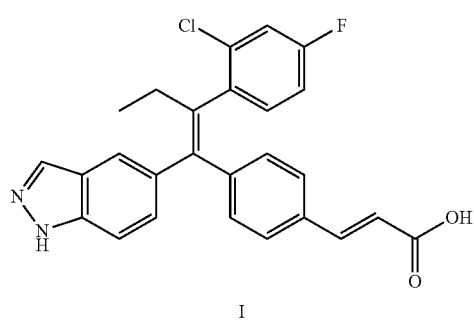

I or

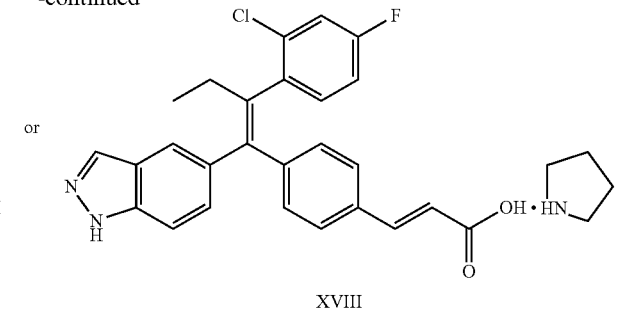

XVIII

Scheme 9 shows conversion of (E)-tert-butyl 3-(4-(2-(2-chloro-4-fluorophenyl)butanoyl)phenyl)acrylate X to (E)-3-(4-((E)-2-(2-chloro-4-fluorophenyl)-1-(1H-indazol-5-yl)but-1-en-1-yl)phenyl)acrylic acid I or pyrrolidin-1-ium (E)-3-(4-((E)-2-(2-chloro-4-fluorophenyl)-1-(1H-indazol-5-yl)but-1-en-1-yl)phenyl)acrylate XVIII (Examples 16-18). The enolate of X was formed with lithium tert-butoxide in THF. Other strong bases such as lithium tert-pentoxide, lithium diisopropylamide and sodium hexamethydisilazide, and other solvents such as methyl t-butyl ether or 2-methyltetrahydrofuran may be used to form the enolate of X. The enolate of X was trapped with para-toluene sulfonic anhydride as (E)-tert-butyl 3-(4-((E)-2-(2-chloro-4-fluorophenyl)-1-(tosyloxy)but-1-en-1-yl)phenyl)acrylate version of XI where E is Ts (tosyl), and a small amount of the undesired Z isomer (Example 16). Other electrophilic reagents may be used, including para-toluenesulfonic anhydride, para-toluenesulfonyl chloride, trifluoromethanesulfonic anhydride, methanesulfonic anhydride, methanesulfonyl chloride and diphenyl phosphoryl chloride to form XI. Coupling of XI and 1-(tetrahydro-2H-pyran-2-yl)-5-(4,4,5,5-tetramethyl-1,3,2-dioxaborolan-2-yl)-1H-indazole XII under palladium catalysis gave IX. Potassium phosphate, sodium hydroxide, and other bases may be used in this reaction. The boronic acid analog of XII, (1-(tetrahydro-2H-pyran-2-yl)-1H-indazol-5-yl)boronic acid, can also be used to couple with XI. Intermediate IX was treated with formic acid and sulfuric acid in water and toluene, or alternatively with aqueous hydrochloric acid and methanol to give (E)-3-(4-((E)-2-(2-chloro-4-fluorophenyl)-1-(1H-indazol-5-yl)but-1-en-1-yl)phenyl)acrylic acid I (Example 17). An alternative isolation involves acid mediated deprotection of Intermediate XI with aqueous acid in toluene, followed by addition of pyrrolidine to give pyrrolidin-1-ium (E)-3-(4-((E)-2-(2-chloro-4-fluorophenyl)-1-(1H-indazol-5-yl)but-1-en-1-yl)phenyl)acrylate XVIII (Example 18).

1)

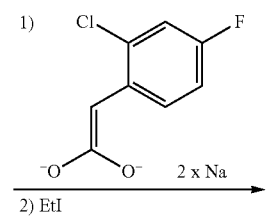

XXI

2) EtI

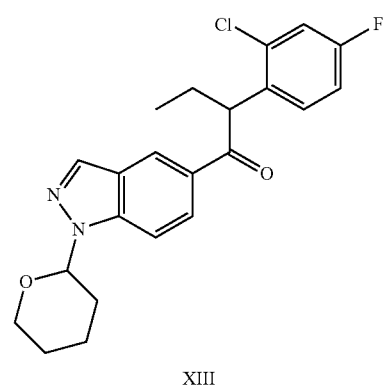

XIII

Scheme 10 shows conversion of 5-bromo-1-(tetrahydro-2H-pyran-2-yl)-1H-indazole VII to 2-(2-chloro-4-fluorophenyl)-1-(1-(tetrahydro-2H-pyran-2-yl)-1H-indazol-5-yl)butan-1-one XIII (Examples 19 and 20).

Scheme 10:

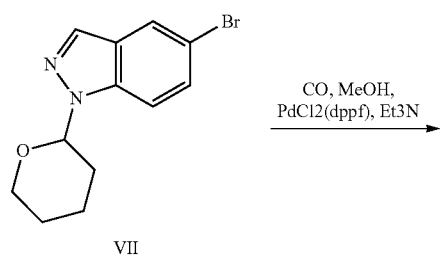

VII

CO, MeOH,
PdCl2(dppf), Et3N
→

Scheme 11:

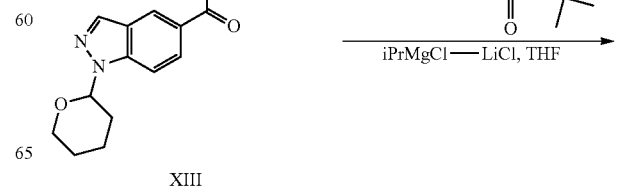

XIII iPrMgCl—LiCl, THF
→

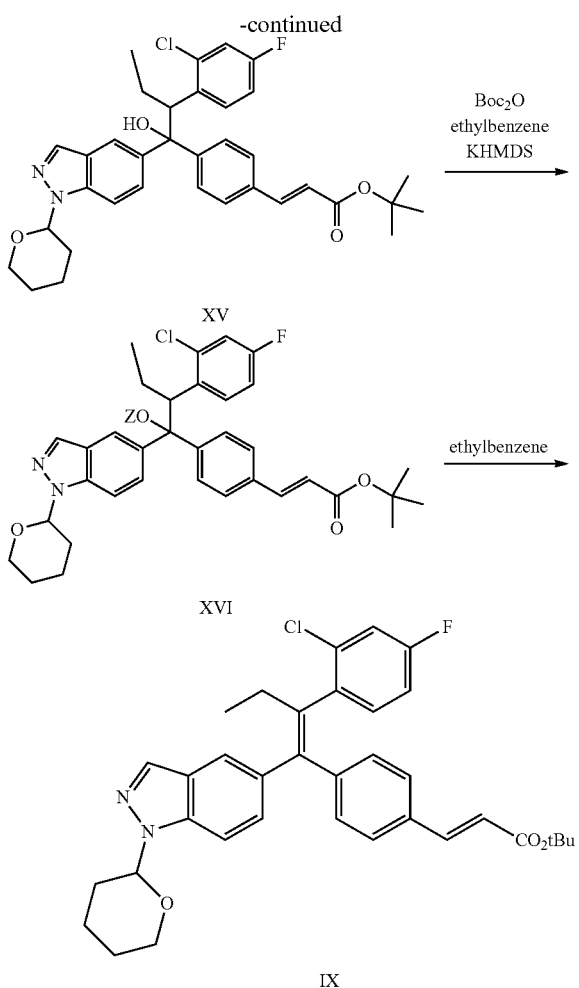

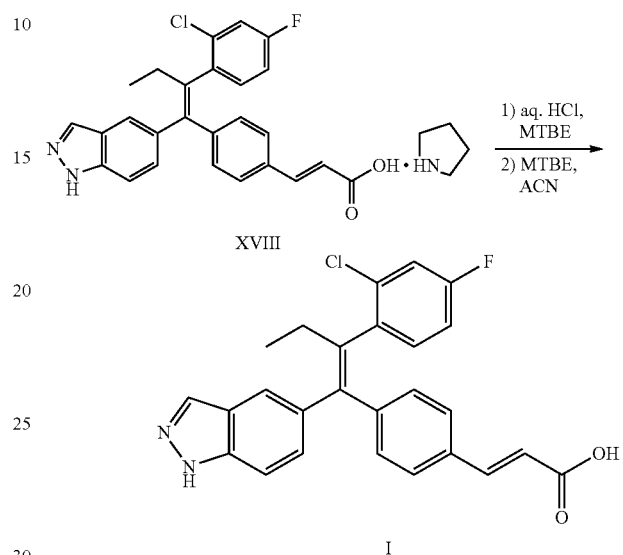

Scheme 11 shows conversion of 2-(2-chloro-4-fluorophenyl)-1-(1-(tetrahydro-2H-pyran-2-yl)-1H-indazol-5-yl)butan-1-one XIII to (E)-3-(4-((E)-2-(2-chloro-4-fluorophenyl)-1-(1H-indazol-5-yl)but-1-en-1-yl)phenyl)acrylic acid I (Examples 21 and 22). The Grignard reagent, (E)-(4-(3-(tert-butoxy)-3-oxoprop-1-en-1-yl)phenyl)magnesium chloride, formed from tert-butyl (E)-3-(4-iodophenyl)acrylate and isopropylmagnesium chloride and lithium chloride complex in THF, adds to XIII to give (E)-tert-butyl 3-(4-(2-(2-chloro-4-fluorophenyl)-1-hydroxy-1-(1-(tetrahydro-2H-pyran-2-yl)-1H-indazol-5-yl)butyl)phenyl)acrylate XV (Example 21). Additives may also be used, including N,N,N',N'-tetramethylethylenediamine and 2,2'-oxybis(N,N-dimethylethan-1-amine) to form Intermediate XV. The tert-butyloxycarbonyl (Boc) ester is formed with di-tert-butyl dicarbonate and Intermediate XV to give the Boc derivative of Intermediate XVI where Z is tert-butyloxycarbonyl (Example 22). Other Z groups include pivaloyl, isopropyl carbonyl, methoxycarbonyl, N,N-dimethyl carbamoyl, diphenylphosphate, isobutoxycarbonyl, acetyl, trifluoroacetyl, trifluoroacetyl bis(2-oxo-3-oxazolidinyl)phosphoryl, diphenylphosphoryl, and diethylphosphoryl. Elimination by heat or under basic conditions gives tetra-substituted olefin IX (Example 22). Other derivatizing agents can be used to form a leaving group, such as pivalate, t-butyl carbonate, isopropyl carbonate, methyl carbonate, N,N-dimethyl carbamate, diphenylphosphate, isobutyl carbonate, acetyl, trifluoroacetyl bis(2-oxo-3-oxazolidinyl)phosphate, and diethylphosphate from the hydroxyl group of XV. Other elimination conditions can be used to form IX. Intermediate IX was treated with formic acid and sulfuric acid in water and toluene, or alternatively with aqueous hydrochloric acid and methanol to give (E)-3-(4-((E)-2-(2-chloro-4-fluorophenyl)-1-(1H-indazol-5-yl)but-1-en-1-yl)phenyl)acrylic acid I (Example 22).

Scheme 12:

Scheme 12 shows conversion of pyrrolidin-1-ium (E)-3-(4-((E)-2-(2-chloro-4-fluorophenyl)-1-(1H-indazol-5-yl)but-1-en-1-yl)phenyl)acrylate XVIII to (E)-3-(4-((E)-2-(2-chloro-4-fluorophenyl)-1-(1H-indazol-5-yl)but-1-en-1-yl)phenyl)acrylic acid I (Example 23).

Scheme 13:

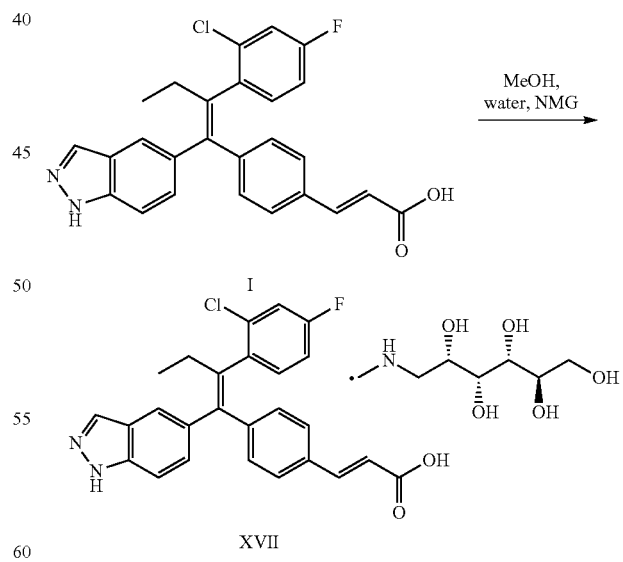

Scheme 13 shows conversion of (E)-3-(4-((E)-2-(2-chloro-4-fluorophenyl)-1-(1H-indazol-5-yl)but-1-en-1-yl)phenyl)acrylic acid I to the NMG salt, (2S,3R,4R,5R)-2,3,4,5,6-pentahydroxy-N-methylhexan-1-aminium (E)-3-(4-((E)-2-(2-chloro-4-fluorophenyl)-1-(1H-indazol-5-yl)but-1-en-1-yl)phenyl)acrylate XVII (Example 24).

Formulations (E)-3-(4-((E)-2-(2-chloro-4-fluorophenyl)-1-(1H-indazol-5-yl)but-1-en-1-yl)phenyl)acrylic acid I (GDC-0810), and salts thereof, may be formulated in accordance with standard pharmaceutical practice for use in a therapeutic combination for therapeutic treatment (including prophylactic treatment) of hyperproliferative disorders in mammals including humans. The invention provides a pharmaceutical composition comprising GDC-0810 in association with one or more pharmaceutically acceptable carrier, glidant, diluent, or excipient.

Suitable carriers, diluents, glidants, and excipients are well known to those skilled in the art and include materials such as carbohydrates, waxes, water soluble and/or swellable polymers, hydrophilic or hydrophobic materials, gelatin, oils, solvents, water and the like.

The formulations may be prepared using conventional dissolution and mixing procedures. The compound of the present invention is typically formulated into pharmaceutical dosage forms to provide an easily controllable dosage of the drug and to enable patient compliance with the prescribed regimen.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Pharmaceutical formulations of the compounds of the present invention may be prepared for various routes and types of administration with pharmaceutically acceptable diluents, carriers, excipients, glidants or stabilizers (Remington's Pharmaceutical Sciences (1995) 18th edition, Mack Publ. Co., Easton, Pa.), in the form of a lyophilized formulation, milled powder, or an aqueous solution. Formulation may be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range from about 3 to about 8.

The pharmaceutical formulation is preferably sterile. In particular, formulations to be used for in vivo administration must be sterile. Such sterilization is readily accomplished by filtration through sterile filtration membranes.

The pharmaceutical formulation ordinarily can be stored as a solid composition, a tablet, a pill, a capsule, a lyophilized formulation or as an aqueous solution.

The pharmaceutical formulations of the invention will be dosed and administered in a fashion, i.e., amounts, concentrations, schedules, course, vehicles and route of administration, consistent with good medical practice. Factors for consideration in this context include the particular disorder being treated, the clinical condition of the individual patient, the cause of the disorder, the site of delivery of the agent, the method of administration, the scheduling of administration, and other factors known to medical practitioners.

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl, ethanol, or benzylalcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as lactose, sucrose, mannitol, trehalose or sorbitol; salt-forming counter-ions such as sodium; metal complexes (e.g., Zn-protein complexes); and/or non-ionic surfactants such as TWEEN™, including Tween 80, PLURONICS™ or polyethylene glycol (PEG), including PEG400. The active pharmaceutical ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 18th edition, (1995) Mack Publ. Co., Easton, Pa. Other examples of drug formulations can be found in Liberman, H. A. and Lachman, L., Eds., Pharmaceutical Dosage Forms, Marcel Decker, Vol 3, $2^{nd}$ Ed., New York, N.Y.

Pharmaceutically acceptable glidants may be selected from silicon dioxide, powdered cellulose, microcrystalline cellulose, metallic stearates, sodium aluminosilicate, sodium benzoate, calcium carbonate, calcium silicate, corn starch, magnesium carbonate, asbestos free talc, stearowet C, starch, starch 1500, magnesium lauryl sulfate, magnesium oxide, and combinations thereof.

The pharmaceutical formulations include those suitable for the administration routes detailed herein. The formulations may conveniently be presented in unit dosage form and may be prepared by any of the methods well known in the art of pharmacy. Techniques and formulations generally are found in Remington's Pharmaceutical Sciences $18^{th}$ Ed. (1995) Mack Publishing Co., Easton, Pa. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Pharmaceutical compositions may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may be a solution or a suspension in a non-toxic parenterally acceptable diluent or solvent, such as a solution in 1,3-butanediol or prepared from a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

EXAMPLES

Example 1 5-bromo-1-(tetrahydro-2H-pyran-2-yl)-1H-indazole VII

To an inerted, 1 L jacketed reactor was added 5-bromo-1H-indazole (CAS Reg. No. 53857-57-1, 40 g, 203 mmol), toluene (200 mL) and p-toluene sulfonic acid monohydrate (0.39 g, 2 mmol) at 15-25° C. The reaction mixture is heated to 65-75° C. and 3,4-dihydro-2H-pyran (18.8 g, 223 mmol) is added over 1 hr and the mixture is stirred for an additional 1 hr at 65-75° C. Once conversion is complete, as deemed by HPLC analysis, 5% aq. sodium bicarbonate (40 g) is charged to the reactor and stirred at 45-55° C. for at least 20 min. Stirring is stopped and the layers are allowed to separate for at least 30 min at 45-55° C. The aqueous layer is removed and water (40 g) is charged to the reactor and stirred at 45-55° C. for at least 20 min. Stirring is stopped and the layers are allowed to separate for at least 30 min at 45-55° C. The aqueous layer is removed and the organic phase is concentrated under vacuum ($T_r$=45-65° C., 350-50 mbar) to remove solvent (145-160 g) to give a concentrated toluene solution of 5-bromo-1-(tetrahydro-2H-pyran-2-yl)-1H-indazole VII (CAS Reg. No. 478828-53-4, 56 g, 199 mmol, 98% yield) (Example 1, WO 2012/037410, Intermediate 1). $^1$H HNR (300 MHz, DMSO-$d_6$): δ 8.10 (s, 1H), 8.02 (d, 1H), 7.73 (d, 1H), 7.53 (dd, 1H), 5.86 (dd, 1H), 3.89-3.85 (m, 1H), 3.73-3.69 (m, 1H), 2.43-2.31 (m, 1H), 2.06-1.92 (m, 2H), 1.80-1.64 (m, 1H), 1.60-1.50 (m, 2H).

Example 2 5-(But-1-yn-1-yl)-1-(tetrahydro-2H-pyran-2-yl)-1H-indazole V

To an inerted, 1 L jacketed reactor was added 5-bromo-1-(tetrahydro-2H-pyran-2-yl)-1H-indazole (56 g, 199 mmol) VII (Example 1, WO 2012/037410, Intermediate 1) as a toluene solution (70-85 g total mass). N,N-dimethylformamide (225 mL) and potassium carbonate (60.6 g, 438.4 mmol) were then charged at 20-30° C., then the reactor was inerted (two vacuum-argon cycles, ≤300 mbar for at least 3-5 minutes vacuum). Copper iodide (0.11 g, 0.57 mmol) and PdCl$_2$(dppf) (0.29 g, 0.40 mmol) were charged to the reaction mixture and the reactor was inerted (two vacuum-argon cycles, ≤300 mbar for at least 3-5 minutes vacuum). 1-butyne (gaseous, 5.5 g, 101.7 mmol) was bubbled through the suspension at <30° C. The reaction mixture was then heated to 85-95° C. while applying a small, constant flow of 1-butyne (gaseous, 21.4 g, 395.6 mmol). After the addition of 1-butyne (total of 2.5 eq., 26.9 g) is complete, then suspension is heated at 85-95° C. for at least 1 hr. Conversion was monitored by HPLC and once the reaction was complete, the mixture was distilled under vacuum (Tr=75-90° C., 150-80 mbar) to remove solvent (50-65 g total). The reaction mixture is cooled to 0-5° C. and 12.5% w/w aq. ammonium hydroxide (30 g) is added dropwise over 20 min. Seeds are charged at 0-5° C. and the mixture is stirred for at least 15 min. Additional 12.5% w/w aq. ammonium hydroxide (270 g) is then added over 1 hr at 0-5° C. and the resulting suspension is stirred for another 30 min. The solids are filtered off and the filter cake is washed with 12.5% w/w aq. ammonium hydroxide (75 g), followed by water (75 g) and finally two heptane (2×51 g) washes. The solids are dried at 35-40° C. to give crude 5-(but-1-yn-1-yl)-1-(tetrahydro-2H-pyran-2-yl)-1H-indazole V (44 g, 165 mmol).

Crude V (44 g, 165 mmol) was charged to a 1 L inerted reactor along with heptane (120 mL) and heated to 55-65° C. for at least 15 min. Water (20 mL) is charged to the reaction mixture and stirred at 55-65° C. for at least 30 min. Stirring is stopped and the layers are allowed to separate for at least 30 min at 45-55° C. The aqueous layer is removed and activated charcoal (4 g) is charged to the reactor and stirred at 60-70° C. for at least 2 hr. The suspension is filtered and washed with heptane (20 mL, hot) and the resulting solution is concentrated under vacuum ($T_r$=50-65° C., 300-100 mbar) to remove solvent (110-120 mL). The concentrated solution is cooled to 30-40° C. and seeded, then stirred for at least 20 min at 30-40° C. The suspension is then cooled to −15 to −5° C. over 1 hr and aged for an additional 1 hr. Solids are filtered off and dried under vacuum at 35-40° C. to give 5-(but-1-yn-1-yl)-1-(tetrahydro-2H-pyran-2-yl)-1H-indazole V (37.4 g, 147 mmol, 74% yield). $^1$H NMR (300 MHz, DMSO-$d_6$): δ 8.08 (s, 1H), 7.82 (s, 1H), 7.69 (d, 1H), 7.39 (d, 1H), 5.84 (dd, 1H), 3.89-3.86 (m, 1H), 3.76-3.72 (m, 1H), 2.45-2.36 (m, 3H), 2.04-1.94 (m, 2H), 1.74 (m, 1H), 1.57-1.20 (m, 2H), 1.16 (t, 3H); LCMS: 255 (M+H)$^+$.

Example 3 (Z)-5-(1,2-bis(4,4,5,5-tetramethyl-1,3,2-dioxaborolan-2-yl)but-1-en-1-yl)-1-(tetrahydro-2H-pyran-2-yl)-1H-indazole VI A 2-methyltetrahydrofuran (MeTHF) solution of 4,4,4',4',5,5,5',5'-octamethyl-2,2'-bi(1,3,2-dioxaborolane) (bis(pinacolato)diboron, B$_2$Pin$_2$, 1.1 equivalents) was added to a 2-methyltetrahydrofuran solution of 5-(but-1-yn-1-yl)-1-(tetrahydro-2H-pyran-2-yl)-1H-indazole V and 0.125 mol % tetrakis(triphenylphosphane)platinum(0) (CAS Reg. No. 14221-02-4) at 90±7° C. over a period of 45 min. After the addition was complete, the reaction mixture was stirred at approx. 90° C. for 2 h, and then cooled to ambient temperature to give (Z)-5-(1,2-bis(4,4,5,5-tetramethyl-1,3,2-dioxaborolan-2-yl)but-1-en-1-yl)-1-(tetrahydro-2H-pyran-2-yl)-1H-indazole VI, characterized in accordance with WO 2012/037411 and Lai et al, (2015) Journal of Medicinal Chemistry, 58(12):4888-4904.

Example 4 (Z)-4-(1-(1-(tetrahydro-2H-pyran-2-yl)-1H-indazol-5-yl)-2-(4,4,5,5-tetramethyl-1,3,2-dioxaborolan-2-yl)but-1-en-1-yl)benzaldehyde IV To a suspension of 2.0 equivalents of cesium carbonate (Cs$_2$CO$_3$) in MeTHF was added 1.5 mol % of bis(triphenylphosphine)palladium(II) dichloride (CAS Reg. No. 13965-03-2, Pd(PPh$_3$)$_2$Cl$_2$), 1.05 equivalents of 4-bromobenzaldehyde (or 4-iodobenzaldehyde) followed by 3.2 equivalents of water. To this mixture was added MeTHF solution of (Z)-5-(1,2-bis(4,4,5,5-tetramethyl-1,3,2-dioxaborolan-2-yl)but-1-en-1-yl)-1-(tetrahydro-2H-pyran-2-yl)-1H-indazole VI at 27±4° C. Upon desired conversion, the reaction was quenched with water. The organic layer was then washed with NH$_4$OH solution and followed by 7%-w/w aqueous NaCl solution. After solvent exchange to CH$_3$CN, the mixture was filtered through activated carbon pad. The filtrate was concentrated to a desired volume to give (Z)-4-(1-(1-(tetrahydro-2H-pyran-2-yl)-1H-indazol-5-yl)-2-(4,4,5,5-tetramethyl-1,3,2-dioxaborolan-2-yl)but-1-en-1-yl)benzaldehyde IV in 55-70% yield over two steps, characterized in accordance with Lai et al, (2015) Journal of Medicinal Chemistry, 58(12):4888-4904.

Example 5 (E)-4-(2-(2-chloro-4-fluorophenyl)-1-(1-(tetrahydro-2H-pyran-2-yl)-1H-indazol-5-yl)but-1-en-1-yl)benzaldehyde III To a mixture of (Z)-4-(1-(1-(tetrahydro-2H-pyran-2-yl)-1H-indazol-5-yl)-2-(4,4,5,5-tetramethyl-1,3,2-dioxaborolan-2-yl)but-1-en-1-yl)benzaldehyde IV, 1.2 equivalents of 2-chloro-4-fluoro-1-iodobenzene, 1.0 mol % palladium acetate (CAS Reg. No. 003375-31-3) and 2.7 mol % triphenylphosphine (CAS #000603-35-0) in THF is added 5.0 equivalents of 15%-w/w aqueous NaOH at 67° C. The reaction mixture stirred at 67° C. for 8-12 h. Upon desired conversion, the phases were allowed to settle and the aqueous layer was separated. The organic phase was diluted with toluene and washed with 5% aqueous NaOH followed by water. The organic phase so obtained was concentrated at atmospheric pressure to a desired volume, and then cooled to ambient temperature to give toluene solution (E)-4-(2-(2-chloro-4-fluorophenyl)-1-(1-(tetrahydro-2H-pyran-2-yl)-1H-indazol-5-yl)but-1-en-1-yl)benzaldehyde III. $^1$H NMR (300 MHz, DMSO-d$_6$): δ 9.82 (s, 1H), 8.15 (s, 1H), 7.78-7.71 (m, 2H), 7.61 (d, 2H), 7.43-7.27 (m, 3H), 7.15 (m, 3H), 5.86 (dd, 1H), 3.93-3.85 (m, 1H), 3.79-3.68 (m, 1H), 2.44-2.36 (m, 3H), 2.10-1.96 (m, 2H), 1.81-1.67 (m, 1H), 1.63-1.53 (m, 2H), 0.92 (t, 3H); LCMS: 405 [(M-THP+H)+H]$^+$.

Example 6 Dicyclohexylammonium (E)-3-(4-((E)-2-(2-chloro-4-fluorophenyl)-1-(1-(tetrahydro-2H-pyran-2-yl)-1H-indazol-5-yl)but-1-en-1-yl)phenyl) acrylate II To a toluene solution of (E)-4-(2-(2-chloro-4-fluorophenyl)-1-(1-(tetrahydro-2H-pyran-2-yl)-1H-indazol-5-yl)but-1-en-1-yl)benzaldehyde III was added 2.0 equivalents of pyridine (CAS Reg. No. 110-86-1) and 0.2 equivalents of piperidine (CAS Reg. NO. 110-89-4) at 23° C. This solution was slowly charged to a suspension of 4.0 equivalents of malonic acid (CAS Reg. No. 141-82-2) in toluene at reflux. The reaction mixture was stirred at reflux until the desired conversion was obtained (<1 h). The reaction was quenched with aqueous sulfuric acid, followed by an aqueous wash of the organic phase. The organic phase was concentrated to a desired under reduced pressure to azeotropically remove residual water. To this reaction mixture was added 1.0 equivalents of dicyclohexylamine DCHA (CAS Reg. No. 101-83-7). The product dicyclohexylammonium (E)-3-(4-((E)-2-(2-chloro-4-fluorophenyl)-1-(1-(tetrahydro-2H-pyran-2-yl)-1H-indazol-5-yl)but-1-en-1-yl)phenyl)acrylate II was then crystallized from a toluene/TBME mixture in 85-92% yield over two steps.

Example 7 (E)-3-(4-((E)-2-(2-chloro-4-fluorophenyl)-1-(1H-indazol-5-yl)but-1-en-1-yl)phenyl)acrylic acid I A mixture of dicyclohexylammonium (E)-3-(4-((E)-2-(2-chloro-4-fluorophenyl)-1-(1-(tetrahydro-2H-pyran-2-yl)-1H-indazol-5-yl)but-1-en-1-yl)phenyl)acrylate II, toluene, and aqueous hydrogen chloride was stirred, followed by treatment with acetic acid (AcOH) and aqueous hydrogen chloride, to give (E)-3-(4-((E)-2-(2-chloro-4-fluorophenyl)-1-(1H-indazol-5-yl)but-1-en-1-yl)phenyl)acrylic acid I.

Alternatively, to a slurry of dicyclohexylammonium (E)-3-(4-((E)-2-(2-chloro-4-fluorophenyl)-1-(1-(tetrahydro-2H-pyran-2-yl)-1H-indazol-5-yl)but-1-en-1-yl)phenyl)acrylate II in toluene was added aqueous H$_2$SO$_4$, to obtain (E)-3-(4-((E)-2-(2-chloro-4-fluorophenyl)-1-(1-(tetrahydro-2H-pyran-2-yl)-1H-indazol-5-yl)but-1-en-1-yl)phenyl)acrylate as solution in toluene. After concentration of this toluene solution to a desired volume, formic acid and concentrated H$_2$SO$_4$ were added to remove the tetrahydropyran (THP) protecting group. Upon desired conversion, the reaction mixture was quenched on to TBME/aqueous NaOH mixture. After aqueous work-up crude product was obtained as a solution in TBME. Solvent exchange to ethanol was followed by addition of acetonitrile to crystallize (E)-3-(4-((E)-2-(2-chloro-4-fluorophenyl)-1-(1H-indazol-5-yl)but-1-en-1-yl)phenyl)acrylic acid I. Filtration and drying provided the desired product (E)-3-(4-((E)-2-(2-chloro-4-fluorophenyl)-1-(1H-indazol-5-yl)but-1-en-1-yl)phenyl)acrylic acid I in 80-85% yield. $^1$H NMR (300 MHz, DMSO-d$_6$): δ 13.12 (s, 1H), 12.34 (br, 1H), 8.11 (d, 1H), 7.69 (s, 1H), 7.56 (d, 1H), 7.44-7.33 (m, 5H), 7.21-7.10 (m, 2H), 6.96 (d, 2H), 6.38 (d, 1H), 2.34 (q, 2H), 0.90 (t, 3H); LCMS: 447 [M+H]$^+$.

Example 8 (E)-tert-butyl 3-(4-((Z)-1-(1-(tetrahydro-2H-pyran-2-yl)-1H-indazol-5-yl)-2-(4,4,5,5-tetramethyl-1,3,2-dioxaborolan-2-yl)but-1-en-1-yl)phenyl) acrylate VIII 4-Bromobenzaldehyde (CAS Reg. No. 1122-91-4), tert-butyl 2-(diethoxyphosphoryl)acetate, lithium chloride, and 1,8-Diazabicyclo[5.4.0]undec-7-ene DBU (CAS Reg. No. 6674-2202) were mixed in acetonitrile to form (E)-tert-butyl 3-(4-bromophenyl)acrylate.

To a 100 mL inerted reactor was added (Z)-5-(1,2-bis(4,4,5,5-tetramethyl-1,3,2-dioxaborolan-2-yl)but-1-en-1-yl)-1-(tetrahydro-2H-pyran-2-yl)-1H-indazole VI (2.89 g, 5.69 mmol), (E)-tert-butyl 3-(4-bromophenyl)acrylate (1.61 g, 5.69 mmol), tetrahydrofuran (8.7 mL), bis(triphenylphosphine)palladium(II) dichloride (0.040 g, 0.057 mmol), cesium carbonate (6.48 g, 19.9 mmol) and water (0.25 mL) at 15-25° C. The reactor was inerted (5-10 min. of bubbling nitrogen through the reaction mixture) and the mixture heated to 60-65° C. for at least 18 hrs. Upon completion based on HPLC analysis, the reaction mixture was cooled to 20° C. 2-methyltetrahydrofuran (50 mL) and water (50 mL) were added and the mixture was stirred for 5-10 min. Stirring was stopped and the layers were allowed to separate for 5-10 min. The aqueous layer was removed, then 2-chloro-4-fluoroiodobenzene (1.75 g, 6.83 mmol), bis(triphenylphosphine)palladium(II) dichloride (0.040 g, 0.057 mmol) and 1.0 M potassium hydroxide (17 mL, 17 mmol) were charged to the reactor. The reactor was inerted (5-10 min. of bubbling nitrogen through the reaction mixture) and the mixture heated to 70° C. for at least 18 hrs. Upon completion based on HPLC analysis, the reaction mixture was cooled to 20° C. The bottom aqueous layer was removed and the organic layer was washed with water (20 mL). The organics were dried with MgSO$_4$, filtered and concentrated under vacuum to give the crude product as dark brown oil. The crude product was purified by silica gel chromatography with a gradient of isopropyl acetate/heptane as eluent, then concentrated under vacuum to give (E)-tert-butyl 3-(4-((E)-2-(2-chloro-4-fluorophenyl)-1-(1-(tetrahydro-2H-pyran-2-yl)-1H-indazol-5-yl)but-1-en-1-yl)phenyl)acrylate IX (2.35 g, 4.0 mmol, 70% yield) as a light yellow oil. $^1$HNMR (300 MHz, DMSO-d$_6$): δ 8.14 (s, 1H), 7.75 (d, 1H), 7.70 (s, 1H), 7.42-7.32 (m, 5H), 7.28 (dt, 1H), 7.14 (td, 1H), 6.95 (s, 1H), 6.92 (s, 1H), 6.36 (d, 1H), 5.86 (dd, 1H), 3.90 (d, 1H), 3.80-3.69 (m, 1H), 2.47-2.31 (m, 3H), 2.11-1.93 (m, 2H), 1.85-1.67 (m, 1H), 1.64-1.53 (m, 2H), 1.44 (s, 9H), 0.90 (t, 3H); LCMS: 587.2 [M+H]$^+$.

Example 9 (E)-3-(4-((E)-2-(2-chloro-4-fluorophenyl)-1-(1H-indazol-5-yl)but-1-en-1-yl)phenyl)acrylic acid I To a 100 mL inerted reactor was added (E)-tert-butyl 3-(4-((E)-2-(2-chloro-4-fluorophenyl)-1-(1-(tetrahydro-2H-pyran-2-yl)-1H-indazol-5-yl)but-1-en-1-yl)phenyl)acrylate IX (5.8 g, 9.87 mmol), toluene (5.0 mL), 98% formic acid (15.0 mL) and 98% sulfuric acid (0.82 mL, 14.8 mmol) at 15-25° C. (Scheme 4). The reaction mixture was stirred at 15-25° C. for at least 4 hr. Upon completion based on HPLC analysis, the reaction mixture was cooled to −20° C. and 25% aqueous sodium hydroxide (54.5 mL) was slowly added, maintaining the temperature at <25° C. Methyl-t-butylether (20 mL) was charged to the reactor and the biphasic mixture was stirred for at least 5-10 min. Stirring was stopped and the layers were allowed to separate for 5-10 min. After removing the aqueous layer, water (10 mL) was charged to the reactor and the mixture was stirred for 5-10 min. Stirring was stopped and the layers were allowed to separate for 5-10 min. The bottom aqueous layer was removed and the organic layer was concentrated (Tr=15-25° C., 200 mbar) to remove solvent. The solvent was exchanged to ethanol (44 mL in total added) during the vacuum distillation, then the reaction mixture was heated to 40° C. Acetonitrile (22.5 mL) was added, followed by seeding and the mixture was stirred at 40° C. for at least 1 hr, then cooled to −10° C. over 2 hr. The solids were filtered off, washed with acetonitrile (10 mL) and dried under vacuum at 50° C. to give (E)-3-(4-((E)-2-(2-chloro-4-fluorophenyl)-1-(1H-indazol-5-yl)but-1-en-1-yl)phenyl)acrylic acid I (2.3 g, 5.1 mmol, 52% yield) as an off-white solid. $^1$H NMR (300 MHz, DMSO-d$_6$): δ 13.12 (s, 1H), 12.34 (br, 1H), 8.11 (d, 1H), 7.69 (s, 1H), 7.56 (d, 1H), 7.44-7.33 (m, 5H), 7.21-7.10 (m, 2H), 6.96 (d, 2H), 6.38 (d, 1H), 2.34 (q, 2H), 0.90 (t, 3H); LCMS: 447 [M+H]$^+$.

Example 10 (E)-tert-butyl 3-(4-(2-(2-chloro-4-fluorophenyl)butanoyl)phenyl)acrylate X To a 500 mL inerted reactor was added sodium hydride (6.6 g, 164.3 mmol, 60 wt % in mineral oil) and tetrahydrofuran (10 mL). This mixture was heated to reflux (about 66° C.) and a solution of methyl 4-bromobenzoate (CAS#619-42-1), (11.7 g, 58.3 mmol), 2-chloro-4-fluorophenylacetic acid (10.0 g, 53.0 mmol) and tetrahydrofuran (40 mL) was added to the reactor over 3 hrs (Scheme 5). This mixture was stirred at reflux for an additional 15 hrs. Upon completion based on HPLC analysis, the mixture was cooled to 40-50° C. Ethanol (20 mL), followed by iodoethane (19.0 g, 121.9 mmol) were charged to the reactor over 1 hr and then the mixture was stirred for an additional 2 hr at 40-50° C. to form 1-(4-bromophenyl)-2-(2-chloro-4-fluorophenyl)butan-1-one XXIII Upon completion based on HPLC analysis, 15% w/w aq. sodium hydroxide (23.5 g) was charged to the reactor and stirred at 40-50° C. for at least 1 hr. Upon completion based on HPLC analysis, concentrated aq. hydrochloric acid (12.5 mL), t-butyl methyl ether (25 mL) and water (10 mL) were charged at 40-50° C. and stirred for at least 10 min. Agitation was stopped and the bottom aqueous layer was removed. 5% w/w aq. sodium bicarbonate (40 mL) was charged and the reaction mixture was stirred at 40-45° C. for at least 30 min. Agitation was stopped and the bottom aqueous layer was removed. The organic phase was distilled under vacuum at 40-50° C. to remove all solvent, then N,N-dimethylacetamide (45 mL) was charged and the mixture was heated to 50-60° C. t-butylacrylate, CAS Reg. No. 1663-39-4 (4.32 g, 33.7 mmol), triethylamine (3.41 g, 33.7 mmol) and 1,1'-bis (diphenylphosphino)ferrocene]dichloropalladium(II) dichloromethane complex (34.4 mg, 0.042 mmol) were charged. The mixture was heated to 90-100° C. and stirred for at least 18 hr. Upon completion based on HPLC analysis, the reaction mixture was cooled to 40-50° C. and ethanol (10 mL) and water (20 mL) were charged and stirred for 30 min. The reaction mixture was cooled further to 20-25° C. over 1 hr and stirred for an additional 30 min. The suspension was filtered, washed with a mixture of ethanol (7.5 mL) and water (2.5 mL) and dried in a vacuum oven at 40° C. for at least 6 hr to provide crude (E)-tert-butyl 3-(4-(2-(2-chloro-4-fluorophenyl)butanoyl)phenyl)acrylate X (10.8 g, 26.8 mmol). The crude solids were charged to a clean reactor along with ethanol (32.4 mL), then heated to 50-60° C. and stirred until all solids dissolved. The reaction mixture was cooled to 40-44° C. over 30 min, seeded (0.5 g) and aged at 40-44° C. for at least 1 hr. The suspension was cooled further to 20-25° C. over 1 hr and water (5 mL) was added over 30 min. The suspension was then cooled to 0-5° C. over 1 hr and aged for at least 15 min. Solids were filtered off, washed with a mixture of ethanol (7.5 mL) and water (2.5 mL), then cold heptane (10 mL) and dried in a vacuum oven at 55° C. for at least 18 hr to give (E)-tert-butyl 3-(4-(2-(2-chloro-4-fluorophenyl)butanoyl)phenyl)acrylate X (9.1 g, 22.6 mmol) as an off-white solid. $^1$HNMR (300 MHz, DMSO-d$_6$): δ 7.92 (s, 1H), 7.89 (s, 1H), 7.82 (s, 1H), 7.79 (s, 1H), 7.56 (d, 1H), 7.49 (dd, 1H), 7.26 (dd, 1H), 7.18 (td, 1H), 6.63 (d, 1H), 5.01 (t, 1H), 2.14-2.00 (m, 1H), 1.81-1.67 (m, 1H), 1.48 (s, 9H), 0.87 (t, 3H).

Example 11 (E)-tert-butyl 3-(4-(2-(2-chloro-4-fluorophenyl)butanoyl)phenyl)acrylate X To a 500 mL inerted reactor was added sodium hydride (13.2 g, 328.6 mmol, 60 wt % in mineral oil) and tetrahydrofuran (20 mL). This mixture was heated to reflux (~66° C.) and a solution of methyl 4-formylbenzoate dimethyl acetal XIX (24.5 g, 116.6 mmol), 2-chloro-4-fluorophenylacetic acid (CAS Reg. No. 177985-32-9) (20.0 g, 106 mmol) and tetrahydrofuran (140 mL) was added to the reactor over 3 hrs. This mixture was stirred at reflux for an additional 6 hrs. Upon completion based on HPLC analysis, the mixture was cooled to 40-50° C. Ethanol (60 mL), followed by iodoethane (38.0 g, 243.8 mmol) were charged to the reactor over 1 hr and then the mixture was stirred for an additional 2 hr at 40-50° C. Upon completion based on HPLC analysis, aqueous hydrochloric acid was added to quench the reaction. Stirring was stopped and the layers were separated. The organic layer was washed with aqueous NaHCO$_3$ and then the solvent was exchanged to toluene using distillation under vacuum to give 4-(2-(2-chloro-4-fluorophenyl)butanoyl)benzaldehyde XX. 15% aqueous NaOH (84.8 g) was charged into the reactor and the contents heated to 40-50° C. Upon complete hydrolysis of ethyl-4-bromobenzoate by HPLC analysis, stirring was stopped and the layers were separated. Additional 15% aqueous NaOH (84.8 g) was charged along with tert-butyldiethylphosphonoacetate (26.8 g, 106 mmol) and N-benzyl-N,N,N-tributylammonium chloride (0.33 g, 1.06 mmol). The reaction mixture was heated at 40-60° C. for 1 hr. Upon completion based on HPLC analysis, the stirring was stopped and the layers were separated. The organic layer was washed with water and the solvent was exchanged to EtOH using distillation under vacuum. The product was crystallized with a mixture of ethanol (39.6 mL) and water (13.2 mL) to give (E)-tert-butyl 3-(4-(2-(2-chloro-4-fluorophenyl)butanoyl)phenyl)acrylate X (20.0 g, 49.8 mmol, 47% yield) as an off-white solid. $^1$H NMR (300 MHz, DMSO-d$_6$): δ 7.92 (s, 1H), 7.89 (s, 1H), 7.82 (s, 1H), 7.79 (s, 1H), 7.56 (d, 1H), 7.49 (dd, 1H), 7.26 (dd, 1H), 7.18 (td, 1H), 6.63 (d, 1H), 5.01 (t, 1H), 2.14-2.00 (m, 1H), 1.81-1.67 (m, 1H), 1.48 (s, 9H), 0.87 (t, 3H).

Example 12 1-(tetrahydro-2H-pyran-2-yl)-5-(4,4,5,5-tetramethyl-1,3,2-dioxaborolan-2-yl)-1H-indazole XII To a 40 L inerted reactor was added a toluene solution of 5-bromo-1-(tetrahydro-2H-pyran-2-yl)-1H-indazole VII (3.0 kg, 10.7 mol, 62% w/w), bis(pinacolato)diboron (3.58 kg, 14.1 mol), [1,1'-Bis(diphenylphosphino)ferrocene]dichloropalladium(II) dichloromethane complex (85.9 g, 0.12 mol), potassium acetate (3.46 kg, 35.2 mol) and toluene (12.0 L). This mixture was heated to 95-105° C. and stirred for at least 20 hr. Upon completion based on HPLC analysis, the mixture was cooled to 20-30° C. The suspension was filtered and the filter cake was washed with toluene (6.0 L). The filtrate was transferred back into the reactor along with 10% aq. N-acetyl cysteine (2.0 kg). The mixture was stirred for at least 30 min, agitation was stopped and the layers were allowed to separate for at least 30 min. The bottom aqueous layer was then removed. 10% aq. sodium carbonate (3.0 kg) was charged and stirred at 25-30° C. for at least 30 min. Agitation was stopped and the layers were allowed to separate for at least 30 min. The bottom aqueous layer was then removed. The organic layers were transferred to a clean container and the combined aqueous layers were transferred back into the reactor along with toluene (3.0 L). The mixture was stirred for at least 30 min, agitation was stopped and the layers were allowed to separate for at least 30 min. The bottom aqueous layer was then removed. The organic layers were combined in the reactor and distilled under vacuum at 50° C. to dryness. Heptane (30 L) was charged to the reactor and the mixture was stirred at 20-25° C. for at least 20 hr. The suspension was filtered, washed with heptane (3.0 L), then dried in a vacuum oven at 50° C. for at least 16 hr to give crude 1-(tetrahydro-2H-pyran-2-yl)-5-(4,4,5,5-tetramethyl-1,3,2-dioxaborolan-2-yl)-1H-indazole XII. The crude solids were slurried with methanol (4.8 L) at 20-25° C. for at least 8 hr. The suspension was then cooled to 5° C. and aged for an additional 12 hr. The solids were filtered off, washed with methanol (1.4 L) and dried in a vacuum oven at 40° C. for at least 24 hr to give crude 1-(tetrahydro-2H-pyran-2-yl)-5-(4,4,5,5-tetramethyl-1,3,2-dioxaborolan-2-yl)-1H-indazole XII. The crude product was subjected to another slurry with methanol (4.8 L) at 20-25° C. for at least 8 hr. The suspension was then cooled to 5° C. and aged for an additional 12 hr. The solids were filtered off, washed with methanol (1.4 L) and dried in a vacuum oven at 40° C. for at least 24 hr to give crude 1-(tetrahydro-2H-pyran-2-yl)-5-(4,4,5,5-tetramethyl-1,3,2-dioxaborolan-2-yl)-1H-indazole XII (1.51 kg, 4.6 mol, 43% yield) as an off-white solid. $^1$H NMR (300 MHz, DMSO-d$_6$): δ 8.16 (d, 2H), 7.69 (dq, 2H), 5.86 (dd, 1H), 3.89 (d, 1H), 3.79-3.69 (m, 1H), 2.48-2.33 (m, 1H), 2.09-1.91 (m, 2H), 1.83-1.67 (m, 1H), 1.63-1.51 (m, 2H), 1.31 (s, 12H); LCMS: 329.2 [M+H]$^+$.

Example 13 1-(tetrahydro-2H-pyran-2-yl)-5-(4,4,5,5-tetramethyl-1,3,2-dioxaborolan-2-yl)-1H-indazole XII To a 1 L inerted reactor was charged THF (100 mL) and n-BuMgCl (47 mL, 94 mmol, 2.0M in THF). n-BuLi (63 mL, 157.5 mmol, 2.5M in hexanes) was slowly charged at 20-25° C. and the mixture was stirred at 20-25° C. for 1 hr to form a white slurry. A THF solution of 5-bromo-1-(tetrahydro-2H-pyran-2-yl)-1H-indazole VII (50 g, 178 mmol, 89% w/w) was slowly charged to the reactor at 20-25° C. and stirred for an additional 2 hr. Upon completion by HPLC analysis, the reaction mixture was slowly transferred to a solution of 2-isopropoxy-4,4,5,5-tetramethyl-1,3,2-dioxaborolane (58.8 g, 316 mmol) in THF (100 mL) at −70 to −60° C. The reaction mixture was warmed to 10-15° C. and stirred for 16 hr. Upon completion by HPLC analysis, aqueous ammonium chloride (200 mL, 15% w/w) was charged to the reactor. Aqueous citric acid (as needed, 5% w/w) was charged to adjust the pH to between 7 and 8. Agitation was stopped and the layers were allowed to separate for at least 30 min. The layers were separated and the aqueous layer was returned to the reactor. Ethyl acetate (300 mL) was charged to the reactor and the contents were stirred for at least 30 min. Agitation was stopped and the layers were allowed to separate for at least 30 min. The bottom aqueous layer was then removed and all organic layers were combined in the reactor, then were distilled under vacuum at 50° C. to dryness. EtOAc (500 mL) and petroleum ether (50 mL) were charged to the reactor to dissolve the crude product. The solution was passed through a silica plug and washed with a mixture of EtOAc (500 mL) and petroleum ether (50 mL). The filtrate was concentrated under vacuum to dryness and dissolved in DMF (50 mL). This solution was heated to 50° C. and water (250 mL) was added dropwise in order to crystallize the product. The suspension was cooled to 20° C. and stirred for 48 hr. The solids were filtered off, then reslurried in heptane (150 mL). Filtration and drying in a vacuum oven gave 1-(tetrahydro-2H-pyran-2-yl)-5-(4,4,5,5-tetramethyl-1,3,2-dioxaborolan-2-yl)-1H-indazole XII (28.0 g, 85.3 mmol, 48% yield) as an off-white solid. $^1$H NMR (300 MHz, DMSO-d$_6$): δ 8.16 (d, 2H), 7.69 (dq, 2H), 5.86 (dd, 1H), 3.89 (d, 1H), 3.79-3.69 (m, 1H), 2.48-2.33 (m, 1H), 2.09-1.91 (m, 2H), 1.83-1.67 (m, 1H), 1.63-1.51 (m, 2H), 1.31 (s, 12H); LCMS: 329.2 [M+H]$^+$.

Example 14 (1-(tetrahydro-2H-pyran-2-yl)-1H-indazol-5-yl)boronic acid XXII

To a 1 L inerted reactor was charged THF (90 mL) and n-BuMgCl (47 mL, 94 mmol, 2.0M in THF). n-BuLi (63 mL, 157.5 mmol, 2.5M in hexanes) was slowly charged at 15-20° C. and the mixture was stirred at 20-25° C. for 20 min to form a white slurry. A THF solution of 5-bromo-1-(tetrahydro-2H-pyran-2-yl)-1H-indazole VII (44.4 g, 158 mmol, 53% w/w) was slowly charged to the reactor at 20-25° C. and stirred for an additional 2.5 hr. Upon completion by HPLC analysis, the reaction mixture was slowly transferred to a solution of trimethyl borate (65 g, 626 mmol) in THF (90 mL) at −70 to −60° C. The reaction mixture was stirred at −70 to −60° C. for 1 hr. Upon completion by HPLC analysis, a mixture of acetic acid (15 mL) and THF (135 mL) was charged to the reactor. The reaction mixture was filtered through silica gel (25 g) and the silica pad was washed with THF (170 mL). The filtrate was concentrated under vacuum to a total volume of 45 mL and dichloromethane (45 mL) was added. Heptane (270 mL) was slowly added to the reactor at 20-25° C. and the slurry was stirred for 16 hr. Filtration and drying in a vacuum oven yielded (1-(tetrahydro-2H-pyran-2-yl)-1H-indazol-5-yl)boronic acid XXII (23.0 g, 93.5 mmol, 59% yield) as an off-white solid. $^1$H NMR (300 MHz, DMSO-d$_6$): δ 8.25 (s, 1H), 8.13 (s, 1H), 8.03 (br, 2H), 7.82 (dd, 1H), 7.66 (d, 1H), 5.83 (dd, 1H), 3.89 (d, 1H), 3.80-3.67 (m, 1H), 2.48-2.34 (m, 1H), 2.10-1.90 (m, 2H), 1.83-1.67 (m, 1H), 1.64-1.53 (m, 2H); LCMS: 247.1 [M+H]$^+$.

Example 15 (1-(tetrahydro-2H-pyran-2-yl)-1H-indazol-5-yl)boronic acid XXII (Scheme 8)

Dissolve 5-bromo-1-(tetrahydro-2H-pyran-2-yl)-1H-indazole VII (50.0 g, 178 mmol, 56% w/w in toluene) in THF (200 mL) in a clean, dry container. Recirculate this solution over dried molecular sieves (54.4 g) until the water content is less than 50 ppm. To a separate clean, dry container, charge triisopropyl borate (43.4 g, 231 mmol) and THF (35 mL). Recirculate this solution over dried molecular sieves (54.4 g) until the water content is less than 50 ppm. In a suitable flow reactor, pump the solution of 5-bromo-1-(tetrahydro-2H-pyran-2-yl)-1H-indazole VII and n-butyllithium (85.4 mL, 214 mmol, 2.5M in hexanes, set pump rate so that the equivalency is 1.2) so that they are well mixed at −30° C. with a residence time of 20 sec. This reaction mixture is then reacted with the solution of triisopropyl borate (set pump rate so that equivalency is 1.3) at −30° C. with a residence time of 30 sec. The effluent from the flow reactor is then transferred into a reactor containing a solution of citric acid (42.8 g, 223 mmol), sodium chloride (43 g) and water (385 mL) that is pre-cooled to 0-5° C. Once all the starting materials have been consumed, stop agitation on the quench vessel and allow the layers to separate. Separate the layers and transfer the bottom aqueous layer back into the reactor. Charge EtOAc (125 mL) and stir at 15-20° C. for 5-10 min. Stop agitation and allow the layers to separate. Separate the layers and transfer the bottom aqueous layer back into the reactor. Charge EtOAc (125 mL) and stir at 15-20° C. for 5-10 min. Stop agitation and allow the layers to separate. Separate the layers and combine the organic layers back into the reactor. Distill under vacuum to obtain a total of ~100 mL. Slowly charge heptane (300 mL) at 20-25° C. and stir for at least 3 hr. Filter the suspension, wash with heptane (50 mL) and dry in a vacuum oven at 50° C. to give (1-(tetrahydro-2H-pyran-2-yl)-1H-indazol-5-yl)boronic acid XXII (28-33 g, 116-134 mmol, 65-75% yield) as an off-white solid. $^1$H NMR (300 MHz, DMSO-d$_6$): δ 8.25 (s, 1H), 8.13 (s, 1H), 8.03 (br, 2H), 7.82 (dd, 1H), 7.66 (d, 1H), 5.83 (dd, 1H), 3.89 (d, 1H), 3.80-3.67 (m, 1H), 2.48-2.34 (m, 1H), 2.10-1.90 (m, 2H), 1.83-1.67 (m, 1H), 1.64-1.53 (m, 2H); LCMS: 247.1 [M+H]$^+$.

Example 16 (E)-tert-butyl 3-(4-((E)-2-(2-chloro-4-fluorophenyl)-1-(tosyloxy)but-1-en-1-yl)phenyl)acrylate XI To a 4 L inerted reactor was added (E)-tert-butyl 3-(4-(2-(2-chloro-4-fluorophenyl)butanoyl)phenyl)acrylate X, (170 g, 422 mmol) and tetrahydrofuran (510 mL) at 15-25° C. and stirred until all solids dissolved. A 1.0 M LiOtBu solution (in THF, 591 mL, 591 mmol) was charged and the reaction mixture was stirred at 15-25° C. for at least 30 min. A separate solution of p-toluenesulfonic anhydride (192.6 g, 591 mmol) in tetrahydrofuran (1.1 L) was prepared and was added to the reaction over 30 min and the reaction mixture was stirred at 15-25° C. for an additional 30 min. Upon completion based on HPLC analysis, the reaction mixture was transferred to a separate reactor containing 5% w/w aq. sodium hydroxide solution (540 mL). This mixture was stirred at 20-25° C. for an additional 30 min. and then the contents were distilled under vacuum at 40-50° C. in order to obtain an overall volume of 680-780 mL. Heptane (1.53 L) was charged and the mixture was stirred at 45-50° C. for at least 15 min. Agitation was stopped and the bottom aqueous layer was removed. Water (340 mL) was charged and the reaction mixture was stirred at 45-50° C. for at least 15 min. Agitation was stopped and the bottom aqueous layer was removed. The organic phase was filtered (Filtrox GF5) and the reactor and filter were washed with heptane (170 mL). The filtrate and wash were transferred to a clean reactor and distilled under vacuum at 45-55° C. to obtain an overall volume of 1.19 L. Heptane (1.02 L) was charged to the reactor. The contents were then distilled under vacuum at 45-50° C. while adding heptane (680 mL) and maintaining a constant volume. Upon completion based on GC analysis, the reactor contents were then heated to 70-80° C. and stirred until all solids were fully dissolved. The solution was cooled to 58-62° C., seeded (17.0 g, 30.5 mmol) and aged for at least 1 hr. The suspension was then cooled further to 0-10° C. over 3 hr and stirred for an additional 1 hr. The suspension was then filtered, washed with cold heptane (340 mL) and dried in a vacuum oven at 50° C. for 8 hr to provide (E)-tert-butyl 3-(4-((E)-2-(2-chloro-4-fluorophenyl)-1-(tosyloxy)but-1-en-1-yl)phenyl)acrylate XI (190.4 g, 341.8 mmol, 81% yield) as an off-white solid. $^1$HNMR (300 MHz, DMSO-d$_6$): δ 7.61 (d, 2H), 7.45-7.31 (m, 6H), 7.12 (dd, 2H), 6.90 (d, 2H), 6.42 (d, 1H), 2.54-2.41 (m, 1H), 2.36 (s, 3H), 2.24 (dd, 1H), 1.46 (s, 9H), 0.75 (t, 3H).

The crude reaction mixture contained E isomer XI and the undesired Z isomer in a ratio of about 20:1. After crystallization, the ratio of E isomer XI and the undesired Z isomer was approximately 45:1 as determined by HPLC analysis.

Example 17 (E)-3-(4-((E)-2-(2-chloro-4-fluorophenyl)-1-(1H-indazol-5-yl)but-1-en-1-yl)phenyl)acrylic acid I To a 1 L inerted reactor was added (E)-tert-butyl 3-(4-((E)-2-(2-chloro-4-fluorophenyl)-1-(tosyloxy)but-1-en-1-yl)phenyl)acrylate XI (37.0 g, 66.4 mmol), 1-(tetrahydro-2H-pyran-2-yl)-5-(4,4,5,5-tetramethyl-1,3,2-dioxaborolan-2-yl)-1H-indazole XII (24.0 g, 73.1 mmol) and dichloro[9,9-dimethyl-4,5-bis(diphenylphosphino)xanthene]palladium (II) (0.38 g, 0.50 mmol). The reactor contents were inerted with three cycles of vacuum and nitrogen breaks. Degassed toluene (290 mL), degassed 28% w/w aq. sodium hydroxide (37.9 g) and water (133 g) were charged to the reactor. The contents were heated to 88-90° C. and stirred for at least 5 hr. Upon completion based on HPLC analysis, the mixture was cooled to 45-55° C. Agitation was stopped and the layers were allowed to separate for at least 10 min. The bottom aqueous layer was removed and water (250 mL) was charged at 40-50° C. The reaction mixture was stirred for 15 min. at 45-50° C., agitation was stopped and the layers were allowed to separate for at least 10 min. The bottom aqueous layer was removed and water (250 mL) was charged at 40-50° C. The reaction mixture was stirred for 15 min. at 45-50° C., agitation was stopped and the layers were allowed to separate for at least 10 min. The bottom aqueous layer was removed and organics were filtered through an activated carbon cartridge (R55, 47 mm). The filtrate was transferred into a clean reactor and the filter was washed with toluene (50 g). The filtrate was distilled under vacuum at 45-50° C. to obtain an overall volume of 190 mL. Formic acid (47.8 g, 98%) and sulfuric acid (13.6 g, 132.8 mmol, 96%) were charged at 15-25° C. The reaction mixture was stirred at 15-25° C. for at least 4 hr. Upon completion based on HPLC analysis, the reaction mixture was cooled to −20° C. and methyl-t-butylether (222 g), 28% aqueous sodium hydroxide (66.5 g) and water (350 g) were slowly added, maintaining the temperature at <25° C. The biphasic mixture was stirred for at least 5-10 min. Stirring was stopped and the layers were allowed to separate for 5-10 min. After removing the aqueous layer, water (200 mL) was charged to the reactor and the mixture was stirred for 5-10 min. Stirring was stopped and the layers were allowed to separate for 5-10 min. After removing the aqueous layer, water (200 mL) was charged to the reactor and the mixture was stirred for 5-10 min. Stirring was stopped and the layers were allowed to separate for 5-10 min. After removing the aqueous layer, the organic layer was concentrated (Tj=60-70° C.) to remove solvent. The solvent was exchanged to ethanol to obtain a final volume of 50-55 mL. Acetonitrile (142 g) was added over 15 min at 60-70° C., followed by seeding and the mixture was stirred at 70° C. for at least 1 hr, then cooled to −10° C. over 8 hr, then aged for an additional 5 hr at −10° C. The solids were filtered off, washed with acetonitrile (100 g) and dried under vacuum at 100° C. to give (E)-3-(4-((E)-2-(2-chloro-4-fluorophenyl)-1-(1H-indazol-5-yl)but-1-en-1-yl)phenyl)acrylic acid I (22.0 g, 49.2 mmol, 74% yield) as an off-white solid. $^1$H NMR (300 MHz, DMSO-$d_6$): δ 13.12 (s, 1H), 12.34 (br, 1H), 8.11 (d, 1H), 7.69 (s, 1H), 7.56 (d, 1H), 7.44-7.33 (m, 5H), 7.21-7.10 (m, 2H), 6.96 (d, 2H), 6.38 (d, 1H), 2.34 (q, 2H), 0.90 (t, 3H); LCMS: 447 [M+H]$^+$.

Example 18 Pyrrolidin-1-ium (E)-3-(4-((E)-2-(2-chloro-4-fluorophenyl)-1-(1H-indazol-5-yl)but-1-en-1-yl)phenyl)acrylate XVIII To a 4 L inerted reactor was added (E)-tert-butyl 3-(4-((E)-2-(2-chloro-4-fluorophenyl)-1-(tosyloxy)but-1-en-1-yl)phenyl)acrylate XI (125.0 g, 224.4 mmol), 1-(tetrahydro-2H-pyran-2-yl)-5-(4,4,5,5-tetramethyl-1,3,2-dioxaborolan-2-yl)-1H-indazole XII (81.0 g, 246.8 mmol) and dichloro[9,9-dimethyl-4,5-bis(diphenylphosphino)xanthene]palladium (II) (1.27 g, 1.68 mmol). The reactor contents were inerted with three cycles of vacuum and nitrogen breaks. Degassed toluene (980 mL), degassed 28% w/w aq. sodium hydroxide (127.5 g) and water (449 g) were charged to the reactor. The contents were heated to 88-90° C. and stirred for at least 5 hr. Upon completion based on HPLC analysis, the mixture was cooled to 45-55° C. Agitation was stopped and the layers were allowed to separate for at least 10 min. The bottom aqueous layer was removed and water (845 mL) was charged at 40-50° C. The reaction mixture was stirred for 15 min. at 45-50° C., agitation was stopped and the layers were allowed to separate for at least 10 min. The bottom aqueous layer was removed and water (845 mL) was charged at 40-50° C. The reaction mixture was stirred for 15 min. at 45-50° C., agitation was stopped and the layers were allowed to separate for at least 10 min. The bottom aqueous layer was removed and organics were filtered through an activated carbon cartridge (R55, 47 mm). The filtrate was transferred into a clean reactor and the filter was washed with toluene (169 mL). The filtrate was distilled under vacuum at 45-50° C. to obtain an overall volume of 640 mL. Formic acid (125 mL, 88% w/w) and sulfuric acid (24.7 mL, 96% w/w) were charged while maintaining the temperature at 15-25° C. The reaction mixture was stirred at 15-25° C. for at least 4 hr. Upon completion based on HPLC analysis, the reaction mixture was cooled to 0-10° C. and 22% aqueous sodium hydroxide (309 mL) was slowly added, maintaining the temperature at <25° C. The reaction mixture was stirred for at least 10 min. Stirring was stopped and the layers were allowed to separate for at least 5 min. After removing the aqueous layer, the organics were distilled under vacuum at 40-50° C. to remove ~250 mL of solvent. Toluene (250 mL) was charged and the distillation under vacuum at 40-50° C. was repeated to remove ~250 mL of solvent. Toluene (200 mL) was charged and the solution was polish filtered into a clean reactor. The lines were washed with toluene (50 mL) and combined with the remaining organic layer. Acetonitrile (375 mL) was charged to the reactor and the contents were heated to 60° C. Pyrrolidine (14.0 mL, 168.3 mmol) was charged to the reactor and the solution was seeded (0.50 g). After aging at 60° C. for at least 10 min, additional pyrrolidine (14.0 mL, 168.3 mmol) were charged over 10 min. The suspension was aged at 60° C. for at least 1 hr, then the contents were cooled to 20° C. over 30 min. The suspension was further aged for at least 1 hr, filtered, washed with acetonitrile (375 mL) and dried in a vacuum oven at 20° C. for 24 hrs to give pyrrolidin-1-ium (E)-3-(4-((E)-2-(2-chloro-4-fluorophenyl)-1-(1H-indazol-5-yl)but-1-en-1-yl)phenyl)acrylate XVIII as an off-white solid. (100.0 g, 193.0 mmol, 86% yield) $^1$H NMR (300 MHz, DMSO-$d_6$): δ 13.17 (br, 1H), 8.10 (d, 1H), 7.68 (s, 1H), 7.55 (d, 1H), 7.35 (dd, 1H), 7.34 (d, 1H), 7.25 (d, 2H), 7.21-7.07 (m, 3H), 6.90 (d, 2H), 6.28 (d, 1H), 2.93 (t, 4H), 2.38 (q, 2H), 1.75-1.68 (m, 4H), 0.90 (t, 3H); LCMS: 447.1 [(M-$C_4H_9N$)+H]$^+$.

Example 19 methyl 1-(tetrahydro-2H-pyran-2-yl)-1H-indazole-5-carboxylate XXI

To a 200 L autoclave was charged sodium acetate (4.03 kg, 49.1 mol), PdCl$_2$(dppf) (0.49 kg, 0.60 mol), a toluene solution of 5-bromo-1-(tetrahydro-2H-pyran-2-yl)-1H-indazole VII (9.3 kg, 33.1 mol, ~60% in toluene) and methanol (75 kg). The reaction mixture was inerted with argon, then pressurized with carbon monoxide (0.8 atm) and heated to 110-120° C. for 22 hr. Upon completion by HPLC analysis, the reaction mixture was cooled to 35-45° C. and concentrated under vacuum to a total volume of 30-37 L. Toluene (40.5 kg) was charged and reaction mixture was distilled under vacuum to a total volume of 30-37 L. Toluene (56.5 kg) and a solution of sodium bicarbonate (3.2 kg), N-acetyl cysteine (2.85 kg) and water (42 kg) were charged and stirred for 1-2 hr at 25-35° C. Agitation was stopped and the layers were allowed to separate for at least 30 min. The bottom aqueous layer was removed, water (150 kg) was charged and the mixture was stirred for at least 30 min. Agitation was stopped and the layers were allowed to separate for at least 30 min. The bottom aqueous layer was removed, and the organic layer was filtered through Celite. The filter cake was washed with toluene (4 kg) and the filtrate was distilled under vacuum to a total volume of 19-38 L. Toluene (40.5 kg) was charged and the mixture was distilled under vacuum to a total volume of 19-38 L. n-Heptane (31.6 kg) was charged over 30 min and the mixture was distilled under vacuum to a total volume of 19-38 L. n-Heptane (31.6 kg) was charged over 30 min. and mixture was distilled under vacuum to a total volume of 19-38 L. n-Heptane (31.6 kg) was charged over 30 min. and mixture was distilled under vacuum to a total volume of 19-38 L. Upon completion of solvent exchange by GC analysis, the reaction mixture was cooled to 15-25° C. and stirred for an additional 45 min. The suspension was filtered and washed with n-heptane (12.4 kg) and dried under vacuum at 50-55° C. to give methyl 1-(tetrahydro-2H-pyran-2-yl)-1H-indazole-5-carboxylate XXI (7.3 kg, 28 mol, 81% yield). $^1$H NMR (300 MHz, DMSO-d$_6$): δ 8.50 (dd, 1H), 8.30 (s, 1H), 8.00 (dd, 1H), 7.84 (d, 1H), 5.91 (dd, 1H), 3.95-3.85 (m, 1H), 3.88 (s, 3H), 3.82-3.71 (m, 1H), 2.47-2.33 (m, 1H), 2.10-1.94 (m, 2H), 1.84-1.66 (m, 1H), 1.64-1.54 (m, 2H); LCMS: 261.1 [M+H]$^+$.

Example 20 2-(2-chloro-4-fluorophenyl)-1-(1-(tetrahydro-2H-pyran-2-yl)-1H-indazol-5-yl)butan-1-one XIII To a 500 mL inerted reactor was added NaHMDS (227.7 mL, 227.7 mmol, 1.0M in THF) and was cooled to −30 to −20° C. A solution of 2-chloro-4-fluorophenyl acetic acid (15.0 g, 79.5 mmol) in tetrahydrofuran (15 mL) was slowly added to the reactor at −30 to −20° C. The reaction mixture was warmed to −5 to 0° C. and stirred for an additional 15 min, then cooled to −30 to −20° C. A solution of methyl 1-(tetrahydro-2H-pyran-2-yl)-1H-indazole-5-carboxylate XXI (30.3 g, 75.5 mmol) in tetrahydrofuran (60 mL) was slowly added to the reactor at −30 to −20° C. The reaction mixture was warmed to 10-15° C. and stirred for an additional 16 hr. Upon completion by HPLC analysis, the mixture was cooled to −30 to −20° C. Ethanol (60 mL) was charged and the reaction was warmed to 10-15° C., then stirred an additional 2 hr. The reaction mixture was cooled to −30 to −20° C. and ethyl iodide (24.8 g, 159 mmol) was charged to the reactor. The reaction mixture was warmed to 15° C. and stirred for an additional 48 hr. Upon completion by HPLC analysis, water (75 mL) was charged at 20-30° C. EtOAc (75 mL) was charged to the reactor and the mixture was stirred for at least 30 min. Agitation was stopped and the layers were separated. The bottom aqueous layer was returned to the reactor along with EtOAc (60 mL) and the mixture was stirred for at least 30 min. Agitation was stopped and the layers were allowed to separate. The organic layers were combined in the reactor and washed with water (75 mL) and 10% aq. NaCl (75 mL). The organics were then distilled under vacuum to dryness to give 2-(2-chloro-4-fluorophenyl)-1-(1-(tetrahydro-2H-pyran-2-yl)-1H-indazol-5-yl)butan-1-one XIII (26 g, 64.9 mmol, 81% yield) as an off-white solid. $^1$H NMR (300 MHz, DMSO-d$_6$): δ 8.50 (s, 1H), 8.31 (s, 1H), 7.95 (dd, 1H), 7.80 (d, 1H), 7.48 (dd, 1H), 7.31 (dd, 1H), 7.18 (dt, 1H), 5.88 (d, 1H), 5.11 (t, 1H), 3.87 (d, 1H), 3.80-3.68 (m, 1H), 2.46-2.29 (m, 1H), 2.19-1.90 (m, 3H), 1.87-1.67 (m, 2H), 1.63-1.52 (m, 2H), 0.89 (t, 3H); LCMS: 401.1 [M+H]$^+$.

Example 21 (E)-tert-butyl 3-(4-(2-(2-chloro-4-fluorophenyl)-1-hydroxy-1-(1-(tetrahydro-2H-pyran-2-yl)-1H-indazol-5-yl)butyl)phenyl)acrylate XV To a 40 mL vial was added tert-butyl (E)-3-(4-iodophenyl)acrylate (1.5 g, 4.5 mmol), 2,2'-oxybis(N,N-dimethylethan-1-amine) (0.7 g, 4.5 mmol) and THF (8 mL). The solution was cooled to −20° C. and isopropylmagnesium chloride lithium chloride complex (4.6 mL, 3.3 mmol, 0.7M in THF) was added over 30 min. This mixture was then stirred at −10° C. for an additional 15 min. To this was added a solution of 2-(2-chloro-4-fluorophenyl)-1-(1-(tetrahydro-2H-pyran-2-yl)-1H-indazol-5-yl)butan-1-one XIII (1.0 g, 2.5 mmol) and THF (3.5 mL) over 15 min at −15 to −5° C. The reaction mixture was warmed to 20-25° C. over 2 hr and stirring continued for an additional 16 hr. Upon completion based on HPLC analysis, saturated aq. NH$_4$Cl (10 mL), MTBE (10 mL) and water (5 mL) were charged and stirred for 5-10 min. Agitation was stopped and the layers were separated. The aqueous layer was extracted with MTBE (10 mL) and the organic layers were combined and concentrated under vacuum at 40° C. to give the crude product, which was purified by silica gel chromatography (40 g, 5-20% IPAC/heptane) to give a pale yellow foam. This solid was dissolved in acetonitrile (20 mL) and seeded to generate a thick slurry. Water (20 mL) was charged over 10 hrs and this suspension was stirred for an additional 6 hr at 20-25° C. The solids were filtered off and dried in a vacuum oven to give (E)-tert-butyl 3-(4-(2-(2-chloro-4-fluorophenyl)-1-hydroxy-1-(1-(tetrahydro-2H-pyran-2-yl)-1H-indazol-5-yl)butyl)phenyl)acrylate XV (1.08 g, 1.8 mmol, 72% yield) as an off-white solid. $^1$H NMR (300 MHz, DMSO-d$_6$): 7.97 (dd, 1H), 7.91 (s, 1H), 7.74-7.65 (m, 4H), 7.62 (d, 1H), 7.54 (d, 1H), 7.35 (dd, 1H), 7.24 (td, 1H), 7.14-7.03 (m, 2H), 6.49 (dd, 1H), 6.18 (d, 1H), 5.70-5.61 (m, 1H), 4.42-4.34 (m, 1H), 3.86-3.74 (m, 1H), 3.70-3.58 (m, 1H), 2.39-2.22 (m, 1H), 2.03-1.90 (m, 1H), 1.90-1.59 (m, 4H), 1.58-1.40 (m, 2H), 1.48 (s, 9H), 0.70 (t, 3H); LCMS: 605.2 [M+H]$^+$.

Example 22 (E)-3-(4-((E)-2-(2-chloro-4-fluorophenyl)-1-(1H-indazol-5-yl)but-1-en-1-yl)phenyl)acrylic acid I To a 100 mL reactor was added (E)-tert-butyl 3-(4-(2-(2-chloro-4-fluorophenyl)-1-hydroxy-1-(1-(tetrahydro-2H-pyran-2-yl)-1H-indazol-5-yl)butyl)phenyl)acrylate XV (5.0 g, 8.3 mmol) and ethyl benzene (35 mL). To this was added a solution of di-tert-butyl dicarbonate (CAS Reg. No. 24424-99-5, 2.7 g, 12.0 mmol) and ethyl benzene (5.0 mL) at 20-25° C. This solution was cooled to 10-15° C. and KHMDS (20 mL, 0.5M in toluene) was added over 30 min and the reaction mixture was stirred for an additional 5 min at 10-15° C. Upon completion based on HPLC analysis, 0.1N NaHCO$_3$ (10 mL) was added and the reaction mixture was stirred for 10 min at 20-25° C. Stirring was stopped and the bottom aqueous layer was removed. 0.1N NaHCO$_3$ (10 mL) was added and the reaction mixture was stirred for 10 min at 20-25° C. Stirring was stopped and the bottom aqueous layer was removed. Water (10 mL) was added and the reaction mixture was stirred for 10 min at 20-25° C. Stirring was stopped and the bottom aqueous layer was removed. The reaction mixture was distilled under vacuum to remove excess water. The reaction mixture was then heated to 130° C. and held for 18-24 hrs. Upon completion based on HPLC analysis, the reaction mixture was cooled to 15-25° C. Formic acid (15.0 mL, 98% w/w) and sulfuric acid (0.82 mL, 14.8 mmol, 96% w/w) were charged at 15-25° C. The reaction mixture was stirred at 15-25° C. for at least 4 hr. Upon completion based on HPLC analysis, the reaction mixture was cooled to −20° C. and 25% aqueous sodium hydroxide (54.5 mL) was slowly added, maintaining the temperature at <25° C. Methyl-t-butylether (20 mL) was charged to the reactor and the biphasic mixture was stirred for at least 5-10 min. Stirring was stopped and the layers were allowed to separate for 5-10 min. After removing the aqueous layer, water (10 mL) was charged to the reactor and the mixture was stirred for 5-10 min. Stirring was stopped and the layers were allowed to separate for 5-10 min. The bottom aqueous layer was removed and the organic layer was concentrated (Tr=15-25° C., 200 mbar) to remove solvent. The solvent was exchanged to ethanol (44 mL in total added) during the vacuum distillation, then the reaction mixture was heated to 40° C. Acetonitrile (22.5 mL) was added, followed by seeding and the mixture was stirred at 40° C. for at least 1 hr, then cooled to −10° C. over 2 hr. The solids were filtered off, washed with acetonitrile (10 mL) and dried under vacuum at 50° C. to give (E)-3-(4-((E)-2-(2-chloro-4-fluorophenyl)-1-(1H-indazol-5-yl)but-1-en-1-yl)phenyl)acrylic acid I (2.3 g, 5.1 mmol, 52% yield) as an off-white solid. $^1$H NMR (300 MHz, DMSO-d$_6$): δ 13.12 (s, 1H), 12.34 (br, 1H), 8.11 (d, 1H), 7.69 (s, 1H), 7.56 (d, 1H), 7.44-7.33 (m, 5H), 7.21-7.10 (m, 2H), 6.96 (d, 2H), 6.38 (d, 1H), 2.34 (q, 2H), 0.90 (t, 3H); LCMS: 447 [M+H]$^+$.

Example 23 (E)-3-(4-((E)-2-(2-chloro-4-fluorophenyl)-1-(1H-indazol-5-yl)but-1-en-1-yl)phenyl)acrylic acid I To a 1 L inerted reactor was charged pyrrolidin-1-ium (E)-3-(4-((E)-2-(2-chloro-4-fluorophenyl)-1-(1H-indazol-5-yl)but-1-en-1-yl)phenyl)acrylate XVIII (103.1 g, 199 mmol), t-butylmethyl ether (586 mL) and 1N hydrochloric acid (206 mL). The reaction mixture was heated to 35-40° C. and stirred until all solids dissolved. Stirring was stopped and the layers were allowed to separate for at least 5 min. After removing the aqueous layer, water (122 g) was charged and the reaction mixture was stirred for at least 5 min. Stirring was stopped and the layers were allowed to separate for at least 5 min. After removing the aqueous layer, the reaction mixture was distilled at 55-65° C. to obtain a final volume of ~120 mL. The temperature was adjusted to 50-55° C. and acetonitrile (303 mL) was charged to the reactor. The solution was seeded (2.5 g), aged at 50-60° C. for at least 2 hr, then cooled to 20° C. over 4 hr. Acetonitrile (425 mL) was charged at 20° C. over 2 hr and the reaction mixture was cooled to −5° C. over 3 hr. The suspension was filtered, washed with acetonitrile (93 mL) and dried in a vacuum oven at 80° C. for 20 hr to give (E)-3-(4-((E)-2-(2-chloro-4-fluorophenyl)-1-(1H-indazol-5-yl)but-1-en-1-yl)phenyl)acrylic acid I (86.4 g, 193 mmol, 97% yield) as an off-white solid. $^1$H NMR (300 MHz, DMSO-d$_6$): δ 13.12 (s, 1H), 12.34 (br, 1H), 8.11 (d, 1H), 7.69 (s, 1H), 7.56 (d, 1H), 7.44-7.33 (m, 5H), 7.21-7.10 (m, 2H), 6.96 (d, 2H), 6.38 (d, 1H), 2.34 (q, 2H), 0.90 (t, 3H); LCMS: 447 [M+H]$^+$.

Example 24 (2S,3R,4R,5R)-2,3,4,5,6-pentahydroxy-N-methylhexan-1-aminium (E)-3-(4-((E)-2-(2-chloro-4-fluorophenyl)-1-(1H-indazol-5-yl)but-1-en-1-yl)phenyl)acrylate XVII To a 250 mL reactor was added (E)-3-(4-((E)-2-(2-chloro-4-fluorophenyl)-1-(1H-indazol-5-yl)but-1-en-1-yl)phenyl)acrylic acid I (20.0 g, 44.8 mmol) and methanol (95.6 g). This mixture was heated to 57-63° C. and stirred until all solids were completely dissolved. The solution was polish filtered through an activated carbon filter and the filter was washed with methanol (2.0 g) at 57-63° C. To this was added a solution of N-methyl-D-glucamine 13.1 g, 67.1 mmol) and water (34.4 g) at 60° C. over 10 min. The solution was cooled to 50° C., seeded and aged for an additional hour at 50° C. The suspension was then cooled to 20° C. over 2 hrs and aged for an additional 18-24 hr at 20° C. The suspension was further cooled to 0° C. over 1 hr and further aged for 18-24 hr at 0° C. The solids were filtered off, washed with methanol (64 g) and dried in a vacuum oven at 120° C. for 24 hr to give (2S,3R,4R,5R)-2,3,4,5,6-pentahydroxy-N-methylhexan-1-aminium (E)-3-(4-((E)-2-(2-chloro-4-fluorophenyl)-1-(1H-indazol-5-yl)but-1-en-1-yl)phenyl)acrylate XVII as a white solid (25.0 g, 39.0 mmol, 87% yield). $^1$H NMR (300 MHz, DMSO-d$_6$): δ 8.10 (d, 1H), 7.69 (s, 1H), 7.56 (d, 1H), 7.36 (dd, 2H), 7.32 (dd, 2H), 7.23-7.09 (m, 3H), 6.92 (d, 2H), 6.32 (d, 1H), 3.86-3.77 (m, 1H), 3.66 (d, 1H), 3.59 (dd, 1H), 3.53-3.34 (m, 3H), 2.91-2.72 (m, 2H), 2.42 (s, 3H), 2.38 (q, 2H), 0.91 (t, 3H); LCMS: 447.1 [(M-C$_7$H$_{17}$NO$_5$)+H]$^+$.

Alternatively, I (50.0 g, 111.9 mmol) and acetone (560 mL, HPLC grade) were charged to a 2 L 3-neck round bottom flask equipped with a mechanical stirrer, a reflux condenser, internal thermometer, and N$_2$ inlet at room temperature. The resulting pale yellow solution was vigorously stirred and heated to 50° C. (internal temperature) in a water bath. N-methyl-D-glucamine (37.3 mL of a 3M aqueous solution, 111.9 mmol) was added dropwise via a syringe over 10 min to the reaction mixture at 50° C. resulting in the formation of a suspension with an oily residue noted the side of the flask.

N-methyl-D-glucamine is also known as methylglucamine; NMG; meglumine; (2R,3R,4R,5S)-6-(methylamino)hexane-1,2,3,4,5-pentol; N-Methylglucamine; 1-Deoxy-1-(methylamino)-D-glucitol; 1-Deoxy-1-methylaminosorbitol; N-Methylsorbitylamine; and Meglumin (CAS Reg. No. 6284-40-8).

The suspension was vigorously stirred for 30 minutes at 50° C. prior to slowly cooling to room temperature with agitation over 2 hours. The suspension was stirred at room temperature for 16 h. The reaction mixture was filtered, collected solid washed with acetone (100 mL, HPLC grade) and dried under vacuum to afford the (E)-3-(4-((E)-2-(2-chloro-4-fluorophenyl)-1-(1H-indazol-5-yl)but-1-en-1-yl)phenyl)acrylic acid, N-methyl glucamine salt XVII as an off-white solid (65.1 g, 91%).

In an alternative embodiment, (E)-3-(4-((E)-2-(2-chloro-4-fluorophenyl)-1-(1H-indazol-5-yl)but-1-en-1-yl)phenyl)acrylic acid (1.0 eq) was dissolved in 4.5 volumes of methanol total at 60° C. N-methyl-D-glucamine (1.3 eq) was dissolved in 1.5 volumes of purified water at 50° C. Half of the N-methyl-D-glucamine solution was then added to the solution of (E)-3-(4-((E)-2-(2-chloro-4-fluorophenyl)-1-(1H-indazol-5-yl)but-1-en-1-yl)phenyl)acrylic acid in methanol at 60° C., and the mixture seeded with previously isolated (E)-3-(4-((E)-2-(2-chloro-4-fluorophenyl)-1-(1H-indazol-5-yl)but-1-en-1-yl)phenyl)acrylic acid N-methyl glucamine salt (form 1). The rest of the N-methyl-D-glucamine solution was then added over 60 minutes at 60° C. The reaction mixture was then stirred for at least an additional 60 minutes maintaining an internal temperature of 50° C., and then cooled over at least 8 hours to an internal temperature of 10° C. The mixture was then stirred for at least a further 1 hour. The suspension was then filtered off, the isolated solid washed with 10° C. methanol (2x 2v), and the solid dried at 120° C. until methanol content was <3000 ppm.

Alternatively, amorphous (E)-3-(4-((E)-2-(2-chloro-4-fluorophenyl)-1-(1H-indazol-5-yl)but-1-en-1-yl)phenyl)acrylic acid, N-methyl glucamine salt XVII is prepared by lyophilizing (E)-3-(4-((E)-2-(2-chloro-4-fluorophenyl)-1-(1H-indazol-5-yl)but-1-en-1-yl)phenyl)acrylic acid I, and N-methyl glucamine salt from water. The resulting material was observed to be a white solid that was confirmed to be amorphous by XRPD analysis.

Crystalline forms of (E)-3-(4-((E)-2-(2-chloro-4-fluorophenyl)-1-(1H-indazol-5-yl)but-1-en-1-yl)phenyl)acrylic acid, N-methyl glucamine salt XVII can be formed by dissolution in an appropriate amount of solvent to create a suspension at room temperature. Appropriate solvents include 1,4 dioxane, toluene, tert-butylmethyl ether (TBME), tetralin, anisole, butyl acetate, ethyl acetate, isopropyl acetate, isopropyl alcohol (IPA), 1,2-dimethoxyethane (DME), dichloromethane (DCM), methyl isobutyl ketone (MIBK), methyl ethyl ketone (MEK), acetone, methanol, ethanol, acetonitrile, and nitromethane. Additionally, MIBK, methanol, and acetonitrile with 5% water was used in further instances. The resulting slurry was then placed in a platform shaker incubator (Heidolph Titramax/Inkubator 1000) and subjected to a series of heat-cool cycles under shaking from room temperature to 50° C. (8 hour cycles: heating to 50° C. for 4 hours and then cooling to room temperature for a further 4 hours) for up to 7 days to obtain a crystalline solid. The resulting solids were confirmed to be crystalline by XRPD analysis.

In other embodiments, amorphous (E)-3-(4-((E)-2-(2-chloro-4-fluorophenyl)-1-(1H-indazol-5-yl)but-1-en-1-yl)phenyl)acrylic acid, N-methyl glucamine salt XVII (ca. 25 mg) was weighed into 1.5 mL vials. About 500 µL of THF (with or without 5% water was added. The resulting slurry was then placed in a platform shaker incubator (Heidolph Titramax/Inkubator 1000) and subjected to a series of heat-cool cycles under shaking from RT to 50° C. (8 hour cycles: heating to 50° C. for 4 hours and then cooling to RT for a further 4 hours) for up to 7 days to obtain an oil. About 250 µL of anti-solvent (heptanes was added) and the solution was subjected to another series of heat-cool cycles under shaking from RT to 50° C. (8 hour cycles: heating to 50° C. for 4 hours and then cooling to RT for a further 4 hours) for 7 days. The resulting solid was confirmed to be crystalline forms of (E)-3-(4-((E)-2-(2-chloro-4-fluorophenyl)-1-(1H-indazol-5-yl)but-1-en-1-yl)phenyl)acrylic acid, N-methyl glucamine salt XVII by XRPD analysis.

In a slow evaporation method, amorphous (E)-3-(4-((E)-2-(2-chloro-4-fluorophenyl)-1-(1H-indazol-5-yl)but-1-en-1-yl)phenyl)acrylic acid, N-methyl glucamine salt XVII (ca. 25 mg) was dissolved with 500 µL of methanol (with or without 5% water) or 1500 acetonitrile. The solution was slowly evaporated at RT to provide a solid, which was confirmed to be crystalline (E)-3-(4-((E)-2-(2-chloro-4-fluorophenyl)-1-(1H-indazol-5-yl)but-1-en-1-yl)phenyl)acrylic acid, N-methyl glucamine salt XVII by XRPD analysis.

In some embodiments, amorphous (E)-3-(4-((E)-2-(2-chloro-4-fluorophenyl)-1-(1H-indazol-5-yl)but-1-en-1-yl)phenyl)acrylic acid, N-methyl glucamine salt (ca. 25 mg) was dissolved with 500 µL of THF or 1,4-dioxane (with 5% water). The solution was slowly evaporated at RT to provide to provide an oil, to which 250 µL of anti-solvent (heptanes) was added and then subjected to a maturation cycle for up to 7 days. The maturation cycle consisted of 8 hour cycles: heating to 50° C. for 4 hours and then cooling to RT for a further 4 hours. Crystalline solid (E)-3-(4-((E)-2-(2-chloro-4-fluorophenyl)-1-(1H-indazol-5-yl)but-1-en-1-yl)phenyl) acrylic acid, N-methyl glucamine salt XVII was confirmed by XRPD analysis.

Cooling was conducted from a super saturated solution of amorphous (E)-3-(4-((E)-2-(2-chloro-4-fluorophenyl)-1-(1H-indazol-5-yl)but-1-en-1-yl)phenyl)acrylic acid, N-methyl glucamine salt prepared by heating the (E)-3-(4-((E)-2-(2-Chloro-4-fluorophenyl)-1-(1H-indazol-5-yl)but-1-en-1-yl)phenyl)acrylic acid, N-methyl glucamine salt in methanol (100 µL) to 65° C. Hot filtering was implemented if necessary to provide a clear solution. The solution was then subjected to an initial cooling period of 16 hours at 4° C. followed overnight cooling at −20° C. If no solid was observed, then 10 µL of an anti-solvent, such as heptanes, was then added and the solution was further cooled at −20° C. for an additional 24 hours. The resulting solid (E)-3-(4-((E)-2-(2-Chloro-4-fluorophenyl)-1-(1H-indazol-5-yl)but-1-en-1-yl)phenyl)acrylic acid, N-methyl glucamine salt was confirmed by XRPD analysis. At 75% relative humidity at 40° C. or 96% relative humidity at 25° C. for 7 days, showed no visible change by XRPD analysis.

Amorphous (E)-3-(4-((E)-2-(2-chloro-4-fluorophenyl)-1-(1H-indazol-5-yl)but-1-en-1-yl)phenyl)acrylic acid, N-methyl glucamine salt (ca. 25 mg) was dissolved with 100 µL of DMSO (with or without 5% water). The solution was slowly evaporated at RT to provide an oil. 250 µL of anti-solvent (heptane) was then added and then subjected to a maturation cycle for up to 7 days. The maturation cycle consisted of 8 hour cycles: heating to 50° C. for 4 hours and then cooling to RT for a further 4 hours. A crystalline solid was obtained and the resulting solid (E)-3-(4-((E)-2-(2-chloro-4-fluorophenyl)-1-(1H-indazol-5-yl)but-1-en-1-yl) phenyl)acrylic acid, N-methyl glucamine salt XVII was confirmed by XRPD analysis.

In some embodiments, approximately 1.5 g of (E)-3-(4-((E)-2-(2-chloro-4-fluorophenyl)-1-(1H-indazol-5-yl)but-1-en-1-yl)phenyl)acrylic acid, N-methyl glucamine salt was lyophilized from 30 mL of water to yield the amorphous (E)-3-(4-((E)-2-(2-chloro-4-fluorophenyl)-1-(1H-indazol-5-yl)but-1-en-1-yl)phenyl)acrylic acid, N-methyl glucamine salt. To the amorphous (E)-3-(4-((E)-2-(2-chloro-4-fluorophenyl)-1-(1H-indazol-5-yl)but-1-en-1-yl)phenyl)acrylic acid, N-methyl glucamine salt was added 20 mL of heptane (anti-solvent) and 100 µL of dimethylsulfoxide (DMSO). The resulting slurry was then placed in a platform shaker incubator (Heidolph Titramax/Inkubator 1000) and subjected to a series of heat-cool cycles under shaking from room temperature to 50° C. (8 hour cycles: heating to 50° C. for 4 hours and then cooling to room temperature for a further 4 hours) for 7 days. The resulting solid (E)-3-(4-((E)-2-(2-chloro-4-fluorophenyl)-1-(1H-indazol-5-yl)but-1-en-1-yl)phenyl)acrylic acid, N-methyl glucamine salt was confirmed by XRPD analysis. Subsequent studies confirmed a DMSO solvate. $^1$HNMR analysis confirmed the presence of DMSO in (E)-3-(4-((E)-2-(2-chloro-4-fluorophenyl)-1-(1H-indazol-5-yl)but-1-en-1-yl)phenyl)acrylic acid, N-methyl glucamine salt XVII. When heated to 110° C. for 10 min and re-analyzed by $^1$HNMR, 0.7 eq of DMSO was still present.

Although the foregoing invention has been described in some detail by way of illustration and example for purposes of clarity of understanding, the descriptions and examples should not be construed as limiting the scope of the invention. Accordingly, all suitable modifications and equivalents may be considered to fall within the scope of the invention as defined by the claims that follow. The disclosures of all patent and scientific literature cited herein are expressly incorporated in their entirety by reference.

What is claimed is:

1. A process for the preparation of (E)-3-(4-((E)-2-(2-chloro-4-fluorophenyl)-1-(1H-indazol-5-yl)but-1-en-1-yl)phenyl)acrylic acid I, comprising:

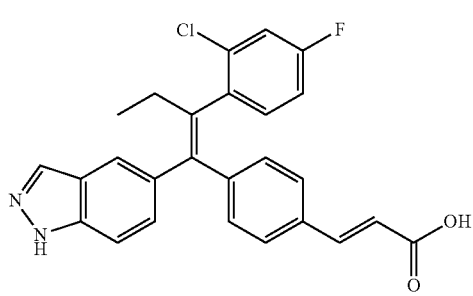

(a) reacting III and malonic acid to form II

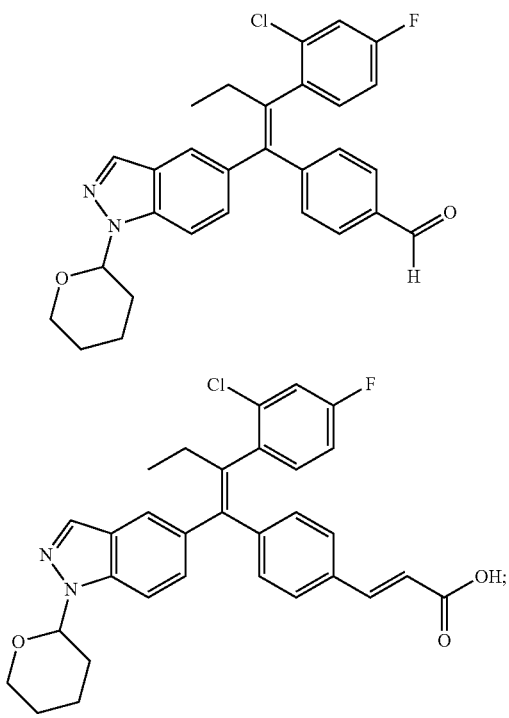

and
(b) reacting II with acid to form I.

2. The process of claim 1 wherein III is prepared by reacting IV:

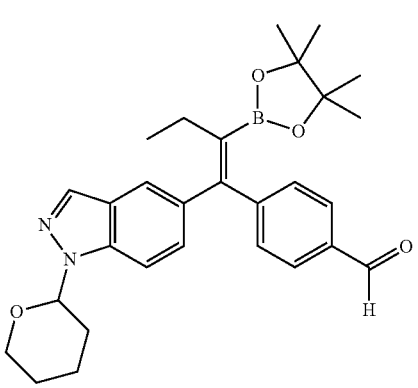

with 2-chloro-4-fluoro-1-iodobenzene and a palladium catalyst.

3. The process of claim 2 wherein the palladium catalyst is selected from $PdCl_2(PPh_3)_2$, $Pd(t-Bu)_3$, $PdCl_2dppf \cdot CH_2Cl_2$, $Pd(PPh_3)_4$, $Pd(OAc)/PPh_3$, $Cl_2Pd[(P(Et_3)]_2$, $Pd(DIPHOS)_2$, $Cl_2Pd(Bipy)$, $[PdCl(Ph_2PCH_2PPh_2)]_2$, $Cl_2Pd[P(o-tol)_3]_2$, $Pd_2(dba)_3/P(o-tol)_3$, $Pd_2(dba)/P(2-furyl)_3$, $Cl_2Pd[P(2-furyl)_3]_2$, $Cl_2Pd(PMePh_2)_2$, $Cl_2Pd[P(4-F-Ph)_3]_2$, $Cl_2Pd[P(C_6F_6)_3]_2$, $Cl_2Pd[P(2-COOH-Ph)(Ph)_2]_2$, $Cl_2Pd[P(4-COOH-Ph)(Ph)_2]_2$, and encapsulated catalysts Pd EnCat™ 30, Pd EnCat™ TPP30, and Pd(II)EnCat™ BINAP30.

4. The process of claim 1 wherein palladium is removed from I with a solid adsorbent palladium scavenger.

5. The process of claim 4 wherein the solid adsorbent palladium scavenger is selected from silica gel, controlled-pore glass, and low cross-linked polystyrene.

6. The process of claim 1 wherein IV is prepared by:
(a) reacting V with 4,4,4',4',5,5,5',5'-octamethyl-2,2'-bi(1,3,2-dioxaborolane) to form VI

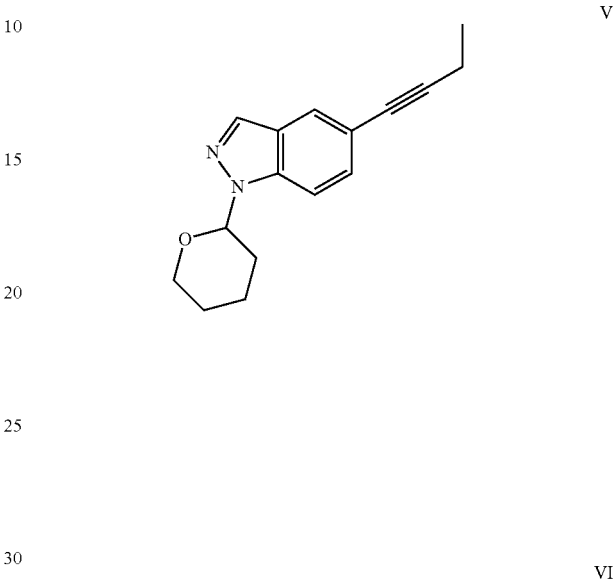

and
(b) reacting VI with 4-iodobenzaldehyde and a palladium catalyst to form IV.

7. The process of claim 1 wherein V is prepared by reacting VII with but-1-yne and a palladium catalyst to form V:

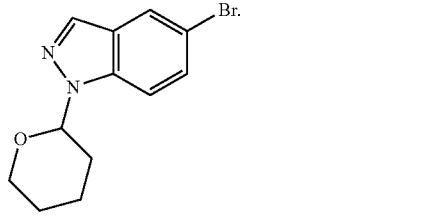

8. The process of claim 1 further comprising forming the NMG salt of I with N-methyl-D-glucamine.

9. A process for (E)-3-(4-((E)-2-(2-chloro-4-fluorophenyl)-1-(1H-indazol-5-yl)but-1-en-1-yl)phenyl)acrylic acid I, comprising:

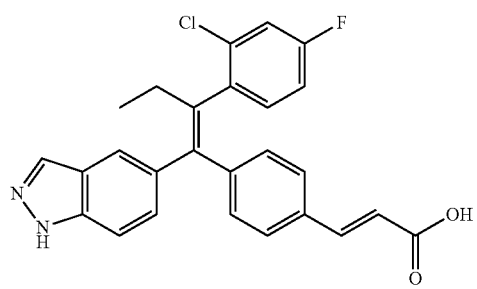

(a) reacting VI and (E)-tert-butyl 3-(4-bromophenyl)acrylate to form VIII

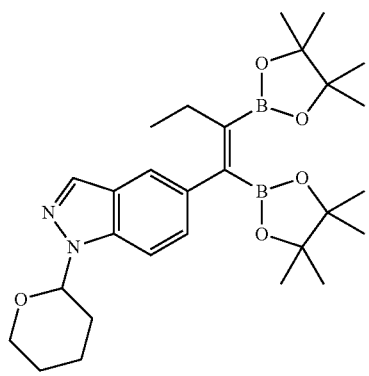

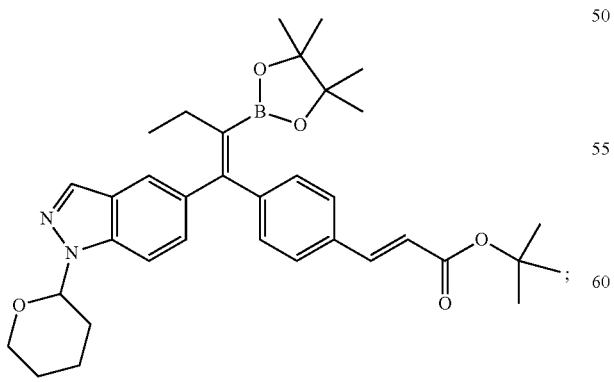

(b) reacting VIII with 2-chloro-4-fluoro-1-iodobenzene to form IX

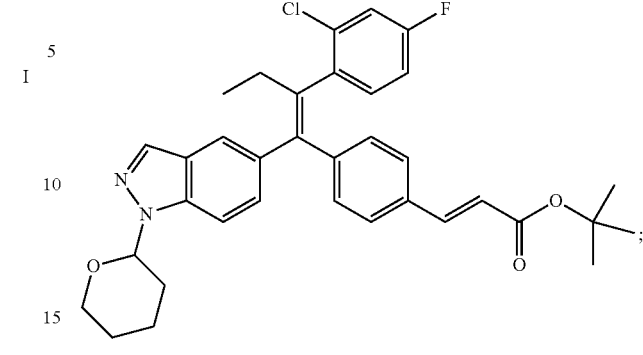

and (c) reacting IX with acid to form I.

10. A process for (E)-3-(4-((E)-2-(2-chloro-4-fluorophenyl)-1-(1H-indazol-5-yl)but-1-en-1-yl)phenyl)acrylic acid I, comprising:

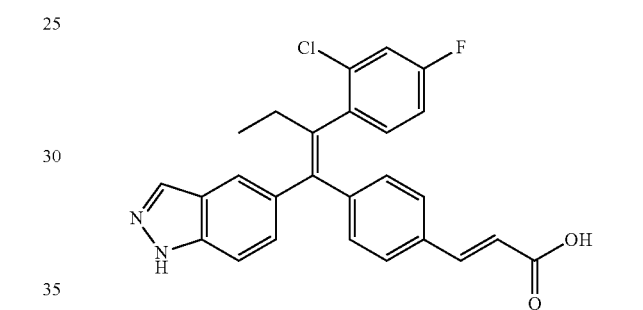

(a) reacting X with an enolization reagent to form XI;

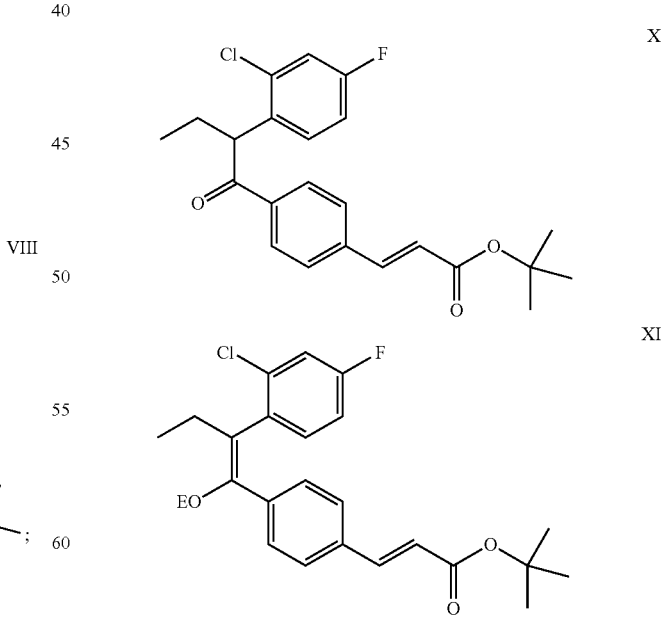

where E is selected from para-toluene sulfonyl, trifluoromethane sulfonyl, methane sulfonyl and diphenyl phosphoryl;

(b) reacting XI with XII and a palladium catalyst to form IX; and

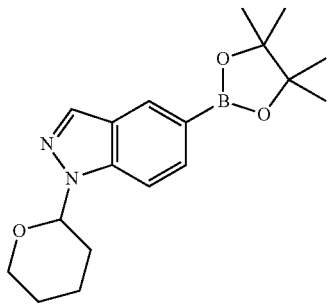

XII

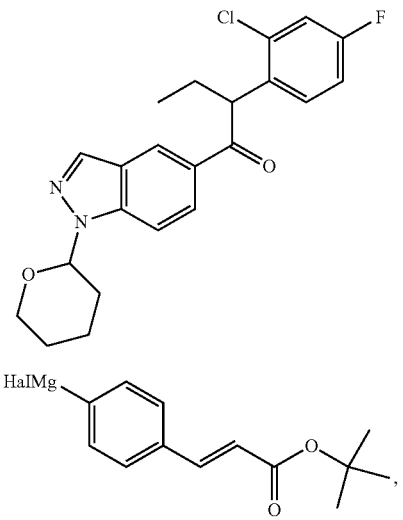

XIII

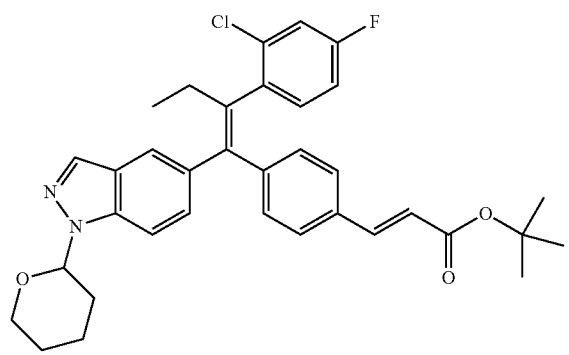

IX (c) reacting IX with aqueous acid to form I.

11. The process of claim 10 wherein the enolization reagent is selected from para-toluenesulfonic anhydride, para-toluenesulfonyl chloride, trifluoromethanesulfonic anhydride, methanesulfonic anhydride, methanesulfonyl chloride and diphenyl phosphoryl chloride.

12. A process for (E)-3-(4-((E)-2-(2-chloro-4-fluorophenyl)-1-(1H-indazol-5-yl)but-1-en-1-yl)phenyl)acrylic acid I, comprising:

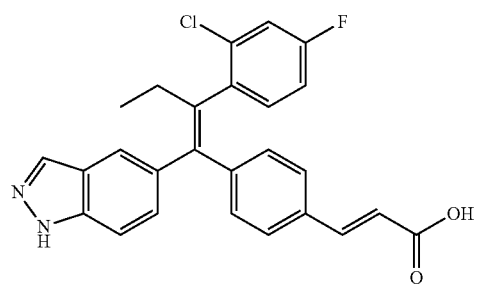

I (a) reacting XIII with (E)-(4-(3-(tert-butoxy)-3-oxoprop-1-en-1-yl)phenyl)magnesium halide reagent XIV to form XV;

XIV where Hal is Cl, Br, or I,

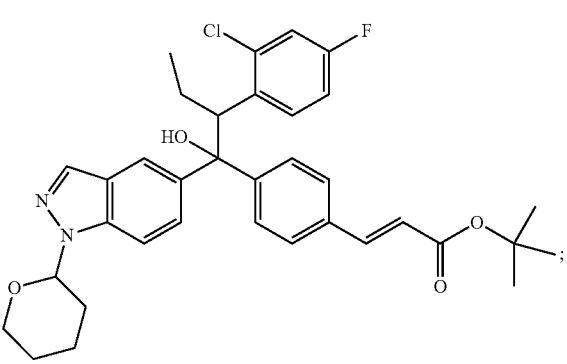

XV (b) reacting XV with a derivatizing reagent to form XVI;

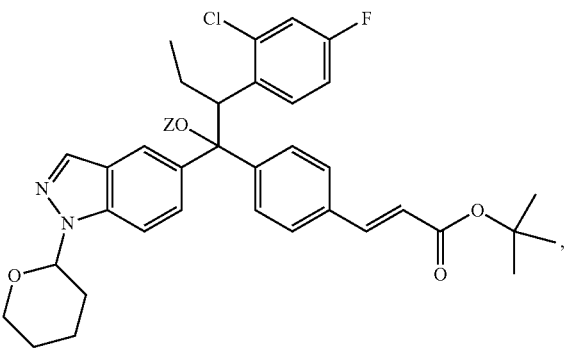

XVI where Z is pivaloyl, t-butoxycarbonyl, isopropyl carbonyl, methoxycarbonyl, N,N-dimethyl carbamoyl, diphenylphosphoryl, isobutyl carbonyl, acetyl, trifluoroacetyl, trifluoroacetyl bis(2-oxo-3-oxazolidinyl) phosphoryl, diphenylphosphoryl, and diethylphosphoryl;

(c) reacting XVI with an elimination reagent selected from sodium hexamethyldisilazide, potassium carbonate, tributylamine, and 1,4-diazabicyclo[2.2.2]octane to form IX

IX

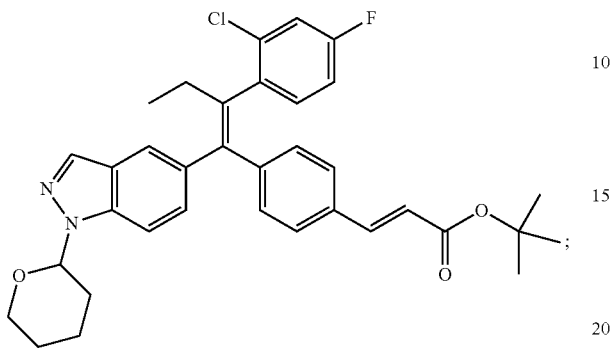

and (d) reacting IX with aqueous acid to form I.

13. The process of claim 11 wherein the derivatizing reagent is selected from pivaloyl chloride, pivaloyl anhydride, di-tert-butyl dicarbonate, isopropyl carbonate, methyl carbonate, N,N-dimethyl carbamoyl chloride, diphenylphosphoryl chloride, isobutyl carbonate, acetic anhydride, trifluoroacetic anhydride, trifluoroacetyl bis(2-oxo-3-oxazolidinyl)phosphoryl chloride, and diethylphosphoryl chloride.

* * * * *